US012746090B2

(12) United States Patent
Defreitas et al.

(10) Patent No.: US 12,746,090 B2
(45) Date of Patent: *Sep. 29, 2026

(54) NEEDLE BREAST BIOPSY SYSTEM AND METHOD OF USE

(71) Applicant: Hologic, Inc., Marlborough, MA (US)

(72) Inventors: Kenneth Defreitas, Patterson, NY (US); Ian Shaw, Marlborough, MA (US); John Laviola, Marlborough, MA (US); Kathleen Pickett, Marlborough, MA (US); Nikolaos A. Gkanatsios, Marlborough, MA (US); Aaron Fand, Marlborough, MA (US); Christopher Ruth, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 17 days.

This patent is subject to a terminal disclaimer.

(21) Appl. No.: 18/966,720

(22) Filed: Dec. 3, 2024

(65) Prior Publication Data

US 2025/0177082 A1 Jun. 5, 2025

Related U.S. Application Data

(63) Continuation of application No. 18/107,113, filed on Feb. 8, 2023, now Pat. No. 12,193,886, which is a (Continued)

(51) Int. Cl.
*A61B 6/12* (2006.01)
*A61B 6/50* (2024.01)
(Continued)

(52) U.S. Cl.
CPC ................ *A61B 90/17* (2016.02); *A61B 6/12* (2013.01); *A61B 10/0233* (2013.01);
(Continued)

(58) Field of Classification Search
CPC ....... A61B 90/17; A61B 6/12; A61B 10/0233; A61B 90/11; A61B 6/502; A61B 34/25;
(Continued)

(56) References Cited

U.S. PATENT DOCUMENTS 3,502,878 A 3/1970 Stewart
3,863,073 A 1/1975 Wagner
(Continued)

FOREIGN PATENT DOCUMENTS

AU 2014339982 4/2015
CN 1802121 A 7/2006
(Continued)

OTHER PUBLICATIONS

European Transmittal of Decision and Summons to attend oral proceedings in EP Application 10707751.3, mailed Jun. 8, 2022, 15 pages.

(Continued)

*Primary Examiner* — Jonathan Cwern
(74) *Attorney, Agent, or Firm* — Merchant & Gould P.C.

(57) ABSTRACT

A tilted needle biopsy assembly is provided for mounting on an x-ray system. Because the biopsy needle is angled relative to at least one of the detector and the x-ray source, x-ray imaging may be performed during the biopsy procedure without interference by the biopsy device. The angled biopsy needle additionally allows improved access to the axilla and chest wall of the patient. The stereotactic biopsy device of the present invention may be coupled to any x-ray system, whether upright or prone, including but not limited to mammography systems, tomosynthesis systems, and combination mammography/tomosynthesis systems. The system flexibly supports the use of any mode of image capture (i.e., scout, two dimensional mammogram, three-dimensional reconstructed volume) for either or both target
(Continued)

visualization and target localization. With such an arrangement, a needle biopsy assembly having improved patient coverage is provided for use with a variety of different x-ray imaging platforms.

20 Claims, 15 Drawing Sheets

Related U.S. Application Data continuation of application No. 16/809,355, filed on Mar. 4, 2020, now Pat. No. 11,701,199, which is a continuation of application No. 12/715,591, filed on Mar. 2, 2010, now Pat. No. 10,595,954.

(60) Provisional application No. 61/249,772, filed on Oct. 8, 2009.

(51) Int. Cl.
*A61B 10/02* (2006.01)
*A61B 90/11* (2016.01)
*A61B 90/17* (2016.01)
*A61B 17/34* (2006.01)
*A61B 34/00* (2016.01)
*A61B 90/00* (2016.01)

(52) U.S. Cl.
CPC ............... *A61B 90/11* (2016.02); *A61B 6/502* (2013.01); *A61B 2017/3409* (2013.01); *A61B 34/25* (2016.02); *A61B 2090/376* (2016.02)

(58) Field of Classification Search
CPC ...... A61B 2017/3409; A61B 2090/376; A61B 6/04; A61B 6/44; A61B 10/02
See application file for complete search history.

(56) References Cited

U.S. PATENT DOCUMENTS

| | | | |
|---|---|---|---|
| 3,971,950 | A | 7/1976 | Evans et al. |
| 4,160,906 | A | 7/1979 | Daniels |
| 4,310,766 | A | 1/1982 | Finkenzeller et al. |
| 4,496,557 | A | 1/1985 | Malen et al. |
| 4,559,557 | A | 12/1985 | Keyes |
| 4,559,641 | A | 12/1985 | Caugant et al. |
| 4,706,269 | A | 11/1987 | Reina et al. |
| 4,727,565 | A | 2/1988 | Ericson |
| 4,744,099 | A | 5/1988 | Huettenrauch |
| 4,773,086 | A | 9/1988 | Fujita |
| 4,773,087 | A | 9/1988 | Plewes |
| 4,819,258 | A | 4/1989 | Kleinman et al. |
| 4,821,727 | A | 4/1989 | Levene et al. |
| 4,907,156 | A | 3/1990 | Doi et al. |
| 4,969,174 | A | 11/1990 | Schied |
| 4,989,227 | A | 1/1991 | Tirelli et al. |
| 5,018,176 | A | 5/1991 | Romeas et al. |
| RE33,634 | E | 7/1991 | Yanaki |
| 5,029,193 | A | 7/1991 | Saffer |
| 5,051,904 | A | 9/1991 | Griffith |
| 5,078,142 | A | 1/1992 | Siczek et al. |
| 5,099,846 | A | 3/1992 | Hardy |
| 5,129,911 | A | 7/1992 | Siczek et al. |
| 5,133,020 | A | 7/1992 | Giger et al. |
| 5,163,075 | A | 11/1992 | Lubinsky |
| 5,164,976 | A | 11/1992 | Scheid et al. |
| 5,199,056 | A | 3/1993 | Darrah |
| 5,219,351 | A | 6/1993 | Teubner |
| 5,240,011 | A | 8/1993 | Assa |
| 5,279,309 | A | 1/1994 | Taylor et al. |
| 5,280,427 | A | 1/1994 | Magnusson |
| 5,289,520 | A | 2/1994 | Pellegrino et al. |
| 5,343,390 | A | 8/1994 | Doi et al. |
| 5,359,637 | A | 10/1994 | Webbe |
| 5,365,562 | A | 11/1994 | Toker |
| 5,386,447 | A | 1/1995 | Siczek |
| 5,415,169 | A | 5/1995 | Siczek et al. |
| 5,426,685 | A | 6/1995 | Pellegrino et al. |
| 5,452,367 | A | 9/1995 | Bick |
| 5,491,627 | A | 2/1996 | Zhang et al. |
| 5,499,097 | A | 3/1996 | Ortyn et al. |
| 5,506,877 | A | 4/1996 | Niklason et al. |
| 5,526,394 | A | 6/1996 | Siczek |
| 5,539,797 | A | 7/1996 | Heidsieck et al. |
| 5,553,111 | A | 9/1996 | Moore |
| 5,592,562 | A | 1/1997 | Rooks |
| 5,594,769 | A | 1/1997 | Pellegrino et al. |
| 5,596,200 | A | 1/1997 | Sharma |
| 5,598,454 | A | 1/1997 | Franetzki |
| 5,609,152 | A | 3/1997 | Pellegrino et al. |
| 5,627,869 | A | 5/1997 | Andrew et al. |
| 5,642,433 | A | 6/1997 | Lee et al. |
| 5,642,441 | A | 6/1997 | Riley et al. |
| 5,647,025 | A | 7/1997 | Frost et al. |
| 5,657,362 | A | 8/1997 | Giger et al. |
| 5,660,185 | A | 8/1997 | Shmulewitz et al. |
| 5,668,889 | A | 9/1997 | Hara |
| 5,671,288 | A | 9/1997 | Wilhelm et al. |
| 5,709,206 | A | 1/1998 | Teboul |
| 5,712,890 | A | 1/1998 | Spivey |
| 5,719,952 | A | 2/1998 | Rooks |
| 5,735,264 | A | 4/1998 | Siczek et al. |
| 5,757,880 | A | 5/1998 | Colomb |
| 5,763,871 | A | 6/1998 | Ortyn et al. |
| 5,769,086 | A | 6/1998 | Ritchart et al. |
| 5,773,832 | A | 6/1998 | Sayed et al. |
| 5,803,912 | A | 9/1998 | Siczek et al. |
| 5,818,898 | A | 10/1998 | Tsukamoto et al. |
| 5,828,722 | A | 10/1998 | Ploetz |
| 5,835,079 | A | 11/1998 | Shieh |
| 5,841,124 | A | 11/1998 | Ortyn et al. |
| 5,872,828 | A | 2/1999 | Niklason et al. |
| 5,875,258 | A | 2/1999 | Ortyn et al. |
| 5,878,104 | A | 3/1999 | Ploetz |
| 5,878,746 | A | 3/1999 | Lemelson et al. |
| 5,896,437 | A | 4/1999 | Ploetz |
| 5,941,832 | A | 8/1999 | Tumey |
| 5,954,650 | A | 9/1999 | Saito |
| 5,986,662 | A | 11/1999 | Argiro |
| 6,005,907 | A | 12/1999 | Ploetz |
| 6,022,325 | A | 2/2000 | Siczek et al. |
| 6,067,079 | A | 5/2000 | Shieh |
| 6,075,879 | A | 6/2000 | Roehrig et al. |
| 6,091,841 | A | 7/2000 | Rogers |
| 6,091,981 | A | 7/2000 | Cundari et al. |
| 6,101,236 | A | 8/2000 | Wang et al. |
| 6,102,866 | A | 8/2000 | Nields et al. |
| 6,137,527 | A | 10/2000 | Abdel-Malek |
| 6,141,398 | A | 10/2000 | He |
| 6,149,301 | A | 11/2000 | Kautzer et al. |
| 6,175,117 | B1 | 1/2001 | Komardin |
| 6,196,715 | B1 | 3/2001 | Nambu |
| 6,215,892 | B1 | 4/2001 | Douglass et al. |
| 6,216,540 | B1 | 4/2001 | Nelson |
| 6,219,059 | B1 | 4/2001 | Argiro |
| 6,233,473 | B1 | 5/2001 | Sheperd |
| 6,243,441 | B1 | 6/2001 | Zur |
| 6,245,028 | B1 | 6/2001 | Furst et al. |
| 6,256,370 | B1 | 7/2001 | Yavus |
| 6,272,207 | B1 | 8/2001 | Tang |
| 6,289,235 | B1 | 9/2001 | Webber et al. |
| 6,292,530 | B1 | 9/2001 | Yavus |
| 6,293,282 | B1 | 9/2001 | Lemelson |
| 6,327,336 | B1 | 12/2001 | Gingold et al. |
| 6,327,377 | B1 | 12/2001 | Rutenberg et al. |
| 6,341,156 | B1 | 1/2002 | Baetz |
| 6,375,352 | B1 | 4/2002 | Hewes |
| 6,389,104 | B1 | 5/2002 | Bani-Hashemi et al. |
| 6,411,836 | B1 | 6/2002 | Patel |
| 6,415,015 | B2 | 7/2002 | Nicolas |
| 6,424,332 | B1 | 7/2002 | Powell |
| 6,442,288 | B1 | 8/2002 | Haerer |
| 6,459,925 | B1 | 10/2002 | Nields et al. |

(56) References Cited

U.S. PATENT DOCUMENTS 6,463,181 B2 10/2002 Duarte
6,468,226 B1 10/2002 McIntyre, IV
6,480,565 B1 11/2002 Ning
6,501,819 B2 12/2002 Unger et al.
6,556,655 B1 4/2003 Chichereau
6,574,304 B1 6/2003 Hsieh
6,597,762 B1 7/2003 Ferrant
6,611,575 B1 8/2003 Alyassin et al.
6,620,111 B2 9/2003 Stephens et al.
6,626,849 B2 9/2003 Huitema et al.
6,633,674 B1 10/2003 Barnes
6,638,235 B2 10/2003 Miller et al.
6,647,092 B2 11/2003 Eberhard
6,650,928 B1 11/2003 Gailly
6,683,934 B1 1/2004 Zhao
6,744,848 B2 6/2004 Stanton
6,748,044 B2 6/2004 Sabol et al.
6,751,285 B2 6/2004 Eberhard
6,758,824 B1 7/2004 Miller et al.
6,813,334 B2 11/2004 Koppe
6,882,700 B2 4/2005 Wang
6,885,724 B2 4/2005 Li
6,901,156 B2 5/2005 Giger et al.
6,912,319 B1 6/2005 Barnes
6,940,943 B2 9/2005 Claus
6,978,040 B2 12/2005 Berestov
6,987,331 B2 1/2006 Koeppe
6,999,553 B2 2/2006 Livingston
6,999,554 B2 2/2006 Mertelmeier
7,022,075 B2 4/2006 Grunwald et al.
7,025,725 B2 4/2006 Dione et al.
7,030,861 B1 4/2006 Westerman
7,110,490 B2 9/2006 Eberhard
7,110,502 B2 9/2006 Tsuji
7,117,098 B1 10/2006 Dunlay et al.
7,123,684 B2 10/2006 Jing et al.
7,127,091 B2 10/2006 OpDeBeek
7,142,633 B2 11/2006 Eberhard
7,218,766 B2 5/2007 Eberhard
7,245,694 B2 7/2007 Jing et al.
7,286,634 B2 10/2007 Sommer, Jr. et al.
7,289,825 B2 10/2007 Fors et al.
7,298,881 B2 11/2007 Giger et al.
7,315,607 B2 1/2008 Ramsauer
7,319,735 B2 1/2008 Defreitas et al.
7,323,692 B2 1/2008 Rowlands
7,346,381 B2 3/2008 Okerlund et al.
7,406,150 B2 7/2008 Minyard et al.
7,430,272 B2 9/2008 Jing et al.
7,443,949 B2 10/2008 Defreitas et al.
7,466,795 B2 12/2008 Eberhard et al.
7,556,602 B2 7/2009 Wang et al.
7,577,282 B2 8/2009 Gkanatsios et al.
7,606,801 B2 10/2009 Faitelson et al.
7,616,801 B2 11/2009 Gkanatsios et al.
7,630,533 B2 12/2009 Ruth et al.
7,634,050 B2 12/2009 Muller et al.
7,640,051 B2 12/2009 Krishnan
7,697,660 B2 4/2010 Ning
7,702,142 B2 4/2010 Ren et al.
7,705,830 B2 4/2010 Westerman et al.
7,760,924 B2 7/2010 Ruth et al.
7,769,219 B2 8/2010 Zahniser
7,787,936 B2 8/2010 Kressy
7,809,175 B2 10/2010 Roehrig et al.
7,828,733 B2 11/2010 Zhang et al.
7,831,296 B2 11/2010 DeFreitas et al.
7,869,563 B2 1/2011 DeFreitas
7,974,924 B2 7/2011 Holla et al.
7,991,106 B2 8/2011 Ren et al.
8,044,972 B2 10/2011 Hall et al.
8,051,386 B2 11/2011 Rosander et al.
8,126,226 B2 2/2012 Bernard et al.
8,155,421 B2 4/2012 Ren et al.
8,165,365 B2 4/2012 Bernard et al.
8,532,745 B2 9/2013 DeFreitas et al.
8,571,289 B2 10/2013 Ruth
8,594,274 B2 11/2013 Hoernig et al.
8,677,282 B2 3/2014 Cragun et al.
8,712,127 B2 4/2014 Ren et al.
8,787,522 B2 7/2014 Smith et al.
8,897,535 B2 11/2014 Ruth et al.
8,983,156 B2 3/2015 Periaswamy et al.
9,020,579 B2 4/2015 Smith
9,075,903 B2 7/2015 Marshall
9,084,579 B2 7/2015 Ren et al.
9,119,599 B2 9/2015 Itai
9,129,362 B2 9/2015 Jerebko
9,289,183 B2 3/2016 Karssemeijer
9,451,924 B2 9/2016 Bernard
9,456,797 B2 10/2016 Ruth et al.
9,478,028 B2 10/2016 Parthasarathy
9,589,374 B1 3/2017 Gao
9,592,019 B2 3/2017 Sugiyama
9,805,507 B2 10/2017 Chen
9,808,215 B2 11/2017 Ruth et al.
9,811,758 B2 11/2017 Ren et al.
9,901,309 B2 2/2018 DeFreitas et al.
10,008,184 B2 6/2018 Kreeger et al.
10,010,302 B2 7/2018 Ruth et al.
10,074,199 B2 9/2018 Robinson et al.
10,092,358 B2 10/2018 DeFreitas
10,111,631 B2 10/2018 Gkanatsios
10,242,490 B2 3/2019 Karssemeijer
10,276,265 B2 4/2019 Reicher et al.
10,282,840 B2 5/2019 Moehrle et al.
10,335,094 B2 7/2019 DeFreitas
10,357,211 B2 7/2019 Smith
10,410,417 B2 9/2019 Chen et al.
10,413,263 B2 9/2019 Ruth et al.
10,444,960 B2 10/2019 Marshall
10,456,213 B2 10/2019 DeFreitas
10,573,276 B2 2/2020 Kreeger et al.
10,575,807 B2 3/2020 Gkanatsios
10,595,954 B2 * 3/2020 DeFreitas .............. A61B 90/11
10,624,598 B2 4/2020 Chen
10,977,863 B2 4/2021 Chen
10,978,026 B2 4/2021 Kreeger
11,419,565 B2 8/2022 Gkanatsios
11,508,340 B2 11/2022 Kreeger
11,701,199 B2 * 7/2023 DeFreitas .......... A61B 10/0233
378/62
12,193,886 B2 * 1/2025 DeFreitas .............. A61B 90/11
2001/0038681 A1 11/2001 Stanton et al.
2001/0038861 A1 11/2001 Hsu et al.
2002/0012450 A1 1/2002 Tsuji
2002/0050986 A1 5/2002 Inoue
2002/0075997 A1 6/2002 Unger et al.
2002/0113681 A1 8/2002 Byram
2002/0122533 A1 9/2002 Marie et al.
2002/0188466 A1 12/2002 Barrette et al.
2002/0193676 A1 12/2002 Bodicker
2003/0007598 A1 1/2003 Wang
2003/0018272 A1 1/2003 Treado et al.
2003/0026386 A1 2/2003 Tang
2003/0048260 A1 3/2003 Matusis
2003/0073895 A1 4/2003 Nields et al.
2003/0095624 A1 5/2003 Eberhard et al.
2003/0097055 A1 5/2003 Yanof
2003/0128893 A1 7/2003 Castorina
2003/0135115 A1 7/2003 Burdette et al.
2003/0169847 A1 9/2003 Karellas
2003/0194050 A1 10/2003 Eberhard
2003/0194121 A1 10/2003 Eberhard et al.
2003/0194124 A1 10/2003 Suzuki et al.
2003/0195433 A1 10/2003 Turovskiy
2003/0210254 A1 11/2003 Doan
2003/0212327 A1 11/2003 Wang
2003/0215120 A1 11/2003 Uppaluri
2004/0008809 A1 1/2004 Webber
2004/0008900 A1 1/2004 Jabri et al.
2004/0008901 A1 1/2004 Avinash
2004/0036680 A1 2/2004 Davis
2004/0047518 A1 3/2004 Tiana

(56) References Cited

U.S. PATENT DOCUMENTS

2004/0052328 A1 3/2004 Saboi
2004/0064037 A1 4/2004 Smith
2004/0066884 A1 4/2004 Claus
2004/0066904 A1 4/2004 Eberhard et al.
2004/0070582 A1 4/2004 Smith et al.
2004/0077938 A1 4/2004 Mark et al.
2004/0081273 A1 4/2004 Ning
2004/0094167 A1 5/2004 Brady
2004/0101095 A1 5/2004 Jing et al.
2004/0109028 A1 6/2004 Stern et al.
2004/0109529 A1 6/2004 Eberhard et al.
2004/0127789 A1 7/2004 Ogawa
2004/0138569 A1 7/2004 Grunwald
2004/0171933 A1 9/2004 Stoller et al.
2004/0171986 A1 9/2004 Tremaglio, Jr. et al.
2004/0267157 A1 12/2004 Miller et al.
2005/0047636 A1 3/2005 Gines et al.
2005/0049521 A1 3/2005 Miller et al.
2005/0063509 A1 3/2005 Defreitas et al.
2005/0078797 A1 4/2005 Danielsson et al.
2005/0084060 A1 4/2005 Seppi et al.
2005/0089205 A1 4/2005 Kapur
2005/0105679 A1 5/2005 Wu et al.
2005/0107689 A1 5/2005 Sasano
2005/0111718 A1 5/2005 MacMahon
2005/0113680 A1 5/2005 Ikeda et al.
2005/0113681 A1 5/2005 DeFreitas et al.
2005/0113715 A1 5/2005 Schwindt et al.
2005/0124845 A1 6/2005 Thomadsen et al.
2005/0135555 A1 6/2005 Claus
2005/0135664 A1 6/2005 Kaufhold
2005/0226375 A1 10/2005 Eberhard
2006/0004278 A1 1/2006 Giger et al.
2006/0009693 A1 1/2006 Hanover et al.
2006/0018526 A1 1/2006 Avinash
2006/0025680 A1 2/2006 Jeune-Lomme
2006/0030784 A1 2/2006 Miller et al.
2006/0074288 A1 4/2006 Kelly et al.
2006/0098855 A1 5/2006 Gkanatsios et al.
2006/0129062 A1 6/2006 Nicoson et al.
2006/0132508 A1 6/2006 Sadikali
2006/0147099 A1 7/2006 Marshall et al.
2006/0154267 A1 7/2006 Ma et al.
2006/0155209 A1 7/2006 Miller et al.
2006/0197753 A1 9/2006 Hotelling
2006/0210131 A1 9/2006 Wheeler
2006/0228012 A1 10/2006 Masuzawa
2006/0238546 A1 10/2006 Handley
2006/0257009 A1 11/2006 Wang
2006/0269040 A1 11/2006 Mertelmeier
2006/0274928 A1 12/2006 Collins et al.
2006/0291618 A1 12/2006 Eberhard et al.
2007/0014468 A1 1/2007 Gines et al.
2007/0019846 A1 1/2007 Bullitt et al.
2007/0030949 A1 2/2007 Jing et al.
2007/0036265 A1 2/2007 Jing et al.
2007/0046649 A1 3/2007 Reiner
2007/0047793 A1 3/2007 Wu et al.
2007/0052700 A1 3/2007 Wheeler et al.
2007/0076844 A1 4/2007 Defreitas et al.
2007/0114424 A1 5/2007 Danielsson et al.
2007/0118400 A1 5/2007 Morita et al.
2007/0156451 A1 7/2007 Gering
2007/0223651 A1 9/2007 Wagenaar et al.
2007/0225600 A1 9/2007 Weibrecht et al.
2007/0236490 A1 10/2007 Casteele
2007/0242800 A1 10/2007 Jing et al.
2007/0263765 A1 11/2007 Wu
2007/0274585 A1 11/2007 Zhang et al.
2008/0019581 A1 1/2008 Gkanatsios et al.
2008/0043905 A1 2/2008 Hassanpourgol
2008/0045833 A1 2/2008 DeFreitas et al.
2008/0101537 A1 5/2008 Sendai
2008/0114614 A1 5/2008 Mahesh et al.
2008/0125643 A1 5/2008 Huisman
2008/0130979 A1 6/2008 Ren
2008/0139896 A1 6/2008 Baumgart
2008/0152086 A1 6/2008 Hall
2008/0165136 A1 7/2008 Christie et al.
2008/0187095 A1 8/2008 Boone et al.
2008/0198966 A1 8/2008 Hjarn
2008/0221479 A1 9/2008 Ritchie
2008/0229256 A1 9/2008 Shibaike
2008/0240533 A1 10/2008 Piron et al.
2008/0297482 A1 12/2008 Weiss
2009/0003519 A1 1/2009 DeFreitas
2009/0005668 A1 1/2009 West et al.
2009/0005693 A1 1/2009 Brauner
2009/0010384 A1 1/2009 Jing et al.
2009/0034684 A1 2/2009 Bernard
2009/0037821 A1 2/2009 O'Neal et al.
2009/0063118 A1 3/2009 Dachille et al.
2009/0079705 A1 3/2009 Sizelove et al.
2009/0080594 A1 3/2009 Brooks et al.
2009/0080602 A1 3/2009 Brooks et al.
2009/0080604 A1 3/2009 Shores et al.
2009/0080752 A1 3/2009 Ruth
2009/0080765 A1 3/2009 Bernard et al.
2009/0087067 A1 4/2009 Khorasani
2009/0123052 A1 5/2009 Ruth
2009/0129644 A1 5/2009 Daw et al.
2009/0135997 A1 5/2009 Defreitas et al.
2009/0138280 A1 5/2009 Morita et al.
2009/0143674 A1 6/2009 Nields
2009/0167702 A1 7/2009 Nurmi
2009/0171244 A1 7/2009 Ning
2009/0238424 A1 9/2009 Arakita
2009/0259958 A1 10/2009 Ban
2009/0268865 A1 10/2009 Ren et al.
2009/0278812 A1 11/2009 Yasutake
2009/0296882 A1 12/2009 Gkanatsios et al.
2009/0304147 A1 12/2009 Jing et al.
2010/0034348 A1 2/2010 Yu
2010/0049046 A1 2/2010 Peiffer
2010/0054400 A1 3/2010 Ren et al.
2010/0067648 A1 3/2010 Kojima
2010/0079405 A1 4/2010 Bernstein
2010/0086188 A1 4/2010 Ruth et al.
2010/0088346 A1 4/2010 Urness et al.
2010/0098214 A1 4/2010 Star-Lack et al.
2010/0105879 A1 4/2010 Katayose et al.
2010/0121178 A1 5/2010 Krishnan
2010/0131294 A1 5/2010 Venon
2010/0131482 A1 5/2010 Linthicum et al.
2010/0135558 A1 6/2010 Ruth et al.
2010/0152570 A1 6/2010 Navab
2010/0166147 A1 7/2010 Abenaim
2010/0166267 A1 7/2010 Zhang
2010/0171764 A1 7/2010 Feng et al.
2010/0189322 A1 7/2010 Sakagawa
2010/0195882 A1 8/2010 Ren et al.
2010/0208037 A1 8/2010 Sendai
2010/0231522 A1 9/2010 Li
2010/0246884 A1 9/2010 Chen et al.
2010/0246909 A1 9/2010 Blum
2010/0259561 A1 10/2010 Forutanpour et al.
2010/0259645 A1 10/2010 Kaplan
2010/0260316 A1 10/2010 Stein et al.
2010/0280375 A1 11/2010 Zhang
2010/0293500 A1 11/2010 Cragun
2011/0018817 A1 1/2011 Kryze
2011/0019891 A1 1/2011 Puong
2011/0054944 A1 3/2011 Sandberg et al.
2011/0069808 A1 3/2011 Defreitas et al.
2011/0069906 A1 3/2011 Park
2011/0087132 A1 4/2011 DeFreitas et al.
2011/0105879 A1 5/2011 Masumoto
2011/0109650 A1 5/2011 Kreeger
2011/0110570 A1 5/2011 Bar-Shalev
2011/0110576 A1 5/2011 Kreeger
2011/0123073 A1 5/2011 Gustafson
2011/0125526 A1 5/2011 Gustafson
2011/0134113 A1 6/2011 Ma et al.
2011/0150447 A1 6/2011 Li

(56) References Cited

U.S. PATENT DOCUMENTS

| | | | |
|---|---|---|---|
| 2011/0157154 | A1 | 6/2011 | Bernard et al. |
| 2011/0163939 | A1 | 7/2011 | Tam et al. |
| 2011/0178389 | A1 | 7/2011 | Kumar et al. |
| 2011/0182402 | A1 | 7/2011 | Partain |
| 2011/0234630 | A1 | 9/2011 | Batman et al. |
| 2011/0237927 | A1 | 9/2011 | Brooks et al. |
| 2011/0242092 | A1 | 10/2011 | Kashiwagi |
| 2011/0310126 | A1 | 12/2011 | Georgiev et al. |
| 2012/0014501 | A1 | 1/2012 | Pelc |
| 2012/0014504 | A1 | 1/2012 | Jang |
| 2012/0014578 | A1 | 1/2012 | Karssemeijer |
| 2012/0069951 | A1 | 3/2012 | Toba |
| 2012/0106698 | A1 | 5/2012 | Karim |
| 2012/0127297 | A1 | 5/2012 | Baxi |
| 2012/0131488 | A1 | 5/2012 | Karlsson et al. |
| 2012/0133600 | A1 | 5/2012 | Marshall |
| 2012/0133601 | A1 | 5/2012 | Marshall |
| 2012/0134464 | A1 | 5/2012 | Hoernig et al. |
| 2012/0148151 | A1 | 6/2012 | Hamada |
| 2012/0150034 | A1 | 6/2012 | DeFreitas et al. |
| 2012/0189092 | A1 | 7/2012 | Jerebko |
| 2012/0194425 | A1 | 8/2012 | Buelow |
| 2012/0238870 | A1 | 9/2012 | Smith et al. |
| 2012/0277625 | A1 | 11/2012 | Nakayama |
| 2012/0293511 | A1 | 11/2012 | Mertelmeier |
| 2013/0016255 | A1 | 1/2013 | Bhatt |
| 2013/0022165 | A1 | 1/2013 | Jang |
| 2013/0044861 | A1 | 2/2013 | Muller |
| 2013/0059758 | A1 | 3/2013 | Haick |
| 2013/0108138 | A1 | 5/2013 | Nakayama |
| 2013/0121569 | A1 | 5/2013 | Yadav |
| 2013/0121618 | A1 | 5/2013 | Yadav |
| 2013/0202168 | A1 | 8/2013 | Jerebko |
| 2013/0259193 | A1 | 10/2013 | Packard |
| 2013/0272494 | A1 | 10/2013 | DeFreitas |
| 2014/0033126 | A1 | 1/2014 | Kreeger |
| 2014/0035811 | A1 | 2/2014 | Guehring |
| 2014/0064444 | A1 | 3/2014 | Oh |
| 2014/0073913 | A1 | 3/2014 | DeFreitas et al. |
| 2014/0082542 | A1 | 3/2014 | Zhang et al. |
| 2014/0200433 | A1 | 7/2014 | Choi |
| 2014/0219534 | A1 | 8/2014 | Wiemker et al. |
| 2014/0219548 | A1 | 8/2014 | Wels |
| 2014/0276061 | A1 | 9/2014 | Lee et al. |
| 2014/0327702 | A1 | 11/2014 | Kreeger et al. |
| 2014/0328517 | A1 | 11/2014 | Gluncic |
| 2015/0004558 | A1 | 1/2015 | Inglese |
| 2015/0052471 | A1 | 2/2015 | Chen |
| 2015/0061582 | A1 | 3/2015 | Tatsui |
| 2015/0238148 | A1 | 8/2015 | Georgescu |
| 2015/0258271 | A1 | 9/2015 | Love |
| 2015/0302146 | A1 | 10/2015 | Marshall |
| 2015/0309712 | A1 | 10/2015 | Marshall |
| 2015/0317538 | A1 | 11/2015 | Ren et al. |
| 2015/0331995 | A1 | 11/2015 | Zhao |
| 2016/0000399 | A1 | 1/2016 | Halmann et al. |
| 2016/0022364 | A1 | 1/2016 | DeFreitas et al. |
| 2016/0051215 | A1 | 2/2016 | Chen |
| 2016/0078645 | A1 | 3/2016 | Abdurahman |
| 2016/0140749 | A1 | 5/2016 | Erhard |
| 2016/0210774 | A1 | 7/2016 | Wiskin et al. |
| 2016/0228034 | A1 | 8/2016 | Gluncic |
| 2016/0235380 | A1 | 8/2016 | Smith |
| 2016/0350933 | A1 | 12/2016 | Schieke |
| 2016/0364526 | A1 | 12/2016 | Reicher et al. |
| 2016/0367210 | A1 | 12/2016 | Gkanatsios |
| 2017/0071562 | A1 | 3/2017 | Suzuki |
| 2017/0132792 | A1 | 5/2017 | Jerebko et al. |
| 2017/0202453 | A1 | 7/2017 | Sekiguchi |
| 2017/0262737 | A1 | 9/2017 | Rabinovich |
| 2018/0008220 | A1 | 1/2018 | Boone et al. |
| 2018/0008236 | A1 | 1/2018 | Venkataraman et al. |
| 2018/0047211 | A1 | 2/2018 | Chen et al. |
| 2018/0109698 | A1 | 4/2018 | Ramsay et al. |
| 2018/0132722 | A1 | 5/2018 | Eggers et al. |
| 2018/0137385 | A1 | 5/2018 | Ren |
| 2018/0144244 | A1 | 5/2018 | Masoud |
| 2018/0256118 | A1 | 9/2018 | DeFreitas |
| 2019/0000318 | A1 | 1/2019 | Caluser |
| 2019/0015173 | A1 | 1/2019 | DeFreitas |
| 2019/0037173 | A1 | 1/2019 | Lee et al. |
| 2019/0043456 | A1 | 2/2019 | Kreeger |
| 2019/0057778 | A1 | 2/2019 | Porter et al. |
| 2019/0287241 | A1 | 9/2019 | Hill et al. |
| 2019/0290221 | A1 | 9/2019 | Smith |
| 2019/0325573 | A1 | 10/2019 | Bernard et al. |
| 2020/0046303 | A1 | 2/2020 | DeFreitas |
| 2020/0054300 | A1 | 2/2020 | Kreeger et al. |
| 2020/0093562 | A1 | 3/2020 | DeFreitas |
| 2020/0184262 | A1 | 6/2020 | Chui |
| 2020/0205928 | A1 | 7/2020 | DeFreitas |
| 2020/0253573 | A1 | 8/2020 | Gkanatsios |
| 2020/0345320 | A1 | 11/2020 | Chen |
| 2020/0390404 | A1 | 12/2020 | DeFreitas |
| 2021/0000553 | A1 | 1/2021 | St. Pierre |
| 2021/0100518 | A1 | 4/2021 | Chui |
| 2021/0100626 | A1 | 4/2021 | St. Pierre |
| 2021/0113167 | A1 | 4/2021 | Chui |
| 2021/0118199 | A1 | 4/2021 | Chui |
| 2021/0174504 | A1 | 6/2021 | Madabhushi |
| 2021/0212665 | A1 | 7/2021 | Tsymbalenko |
| 2022/0005277 | A1 | 1/2022 | Chen |
| 2022/0013089 | A1 | 1/2022 | Kreeger |
| 2022/0036545 | A1 | 2/2022 | St. Pierre |
| 2022/0192615 | A1 | 6/2022 | Chui |
| 2022/0254023 | A1 | 8/2022 | McKinney et al. |
| 2022/0386969 | A1 | 12/2022 | Smith |
| 2023/0000467 | A1 | 1/2023 | Shi |
| 2023/0008465 | A1 | 1/2023 | Smith |
| 2023/0033601 | A1 | 2/2023 | Chui |
| 2023/0038498 | A1 | 2/2023 | Xu |
| 2023/0053489 | A1 | 2/2023 | Kreeger |
| 2023/0054121 | A1 | 2/2023 | Chui |
| 2023/0056692 | A1 | 2/2023 | Gkanatsios |
| 2023/0082494 | A1 | 3/2023 | Chui |
| 2023/0098305 | A1 | 3/2023 | St. Pierre |
| 2023/0103969 | A1 | 4/2023 | St. Pierre |
| 2023/0124481 | A1 | 4/2023 | St. Pierre |
| 2023/0125385 | A1 | 4/2023 | Solis |
| 2023/0225821 | A1 | 7/2023 | DeFreitas |
| 2023/0230679 | A1 | 7/2023 | Chen |
| 2023/0240785 | A1 | 8/2023 | DeFreitas |
| 2023/0344453 | A1 | 10/2023 | Yang |
| 2023/0394769 | A1 | 12/2023 | Chen |
| 2024/0169958 | A1 | 5/2024 | Kreeger |
| 2024/0315654 | A1 | 9/2024 | Chui |
| 2024/0320827 | A1 | 9/2024 | Chui |

FOREIGN PATENT DOCUMENTS

| | | | |
|---|---|---|---|
| CN | 1846622 | | 10/2006 |
| CN | 101066212 | A | 11/2007 |
| CN | 102169530 | A | 8/2011 |
| CN | 202161328 | | 3/2012 |
| CN | 102429678 | | 5/2012 |
| CN | 102473300 | A | 5/2012 |
| CN | 105193447 | | 12/2015 |
| CN | 106659468 | A | 5/2017 |
| CN | 107440730 | | 12/2017 |
| CN | 112561908 | A | 3/2021 |
| DE | 102010009295 | | 8/2011 |
| DE | 102011087127 | | 5/2013 |
| EP | 775467 | | 5/1997 |
| EP | 982001 | | 3/2000 |
| EP | 1428473 | | 6/2004 |
| EP | 2236085 | | 6/2010 |
| EP | 2215600 | | 8/2010 |
| EP | 2301432 | | 3/2011 |
| EP | 2491863 | | 8/2012 |
| EP | 1986548 | | 1/2013 |
| EP | 2656789 | | 10/2013 |
| EP | 2823464 | | 1/2015 |
| EP | 2823765 | | 1/2015 |
| EP | 2889743 | | 7/2015 |

(56) References Cited

FOREIGN PATENT DOCUMENTS

| | | |
|---|---|---|
| EP | 3060132 | 4/2019 |
| JP | H09-35043 | 2/1997 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |
| JP | 2008-068032 | 3/2008 |
| JP | 2008518684 | 6/2008 |
| JP | 2008-253401 | 10/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-530768 | 8/2013 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2016059743 | 4/2016 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005051197 | 6/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 2008/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

Canadian Office Action in Application 2829349, mailed Oct. 15, 2018, 4 pages.

Chinese 2nd Office Action in Application 201480058064.5, mailed Jul. 16, 2019, 5 pgs.

Chinese office action dated Apr. 16, 2019 for Chinese Patent Application No. 201480014655.2, in Chinese with English translation provided by Chinese associate, 27 pages.

Chinese office action dated Mar. 1, 2018 for Chinese Patent Application No. 201480014655.2, in Chinese with English translation provided by Chinese associate, 18 pages.

Chinese office action dated Sep. 18, 2018 for Chinese Patent Application No. 201480014655.2, in Chinese with English translation provided by Chinese associate, 27 pages.

European Communication in Application 10707751.3, mailed Oct. 4, 2018, 5 pages.

European Communication in Application 10707751.3, mailed Aug. 7, 2019, 6 pages.

European Communication of a Notice of Opposition in Application 10707751.3, mailed Sep. 13, 2021, 23 pages.

European Extended Search Report dated Jul. 18, 2014 in EP App 12754521.8, 7 pages.

European Extended Search Report for European Patent Application No. 14770362.3 mailed Sep. 28, 2016, 8 pgs.

European Extended Search Report in Application 14855181.5, mailed May 15, 2017, 7 pages.

European extended Search Report in Application 18153706.9, mailed Jun. 1, 2018, 8 pages.

European Mar. 23, 2009 European Search Report in connection with counterpart European patent Application No. 07750818.

European Office Action in Application 10707751.3, mailed Feb. 19, 2018, 5 pgs.

Japanese Notice of Final Rejection in Application 2016-526115, mailed Jun. 24, 2019, 5 pages.

Observations by Third Party, Remarks concerning European patent application No. 10707751.3 according to Article 115 EPC, dated Apr. 24, 2014, 8 pgs.

PCT Feb. 20, 2008 International Search Report and Written Opinion in connection with corresponding International patent application No. PCT/US2007/04006, 7 pgs.

PCT International Preliminary Report on Patentability in International Application PCT/US2014/061994, mailed Apr. 26, 2016, 5 pages.

PCT International Search Report and Written Opinion in Application PCT/US2010/025873, dated Aug. 2, 2010, 19 pgs.

(56) References Cited

OTHER PUBLICATIONS

PCT International Search Report in Application PCT/US2014/026164, mailed Jul. 28, 2014, 1 page.
PCT International Written Report for International Application PCT/US2014/026164, mailed Jul. 28, 2014, 2 pgs.
PCT Written Opinion in International Application PCT/US2014/061994, mailed Jan. 22, 2015, 4 pages.
PCT/US12/28334 International Search Report and Written Opinion, dated Jul. 5, 2012, 7 pages.
"Filtered Back Projection", (NYGREN), published May 8, 2007, URL: http://web.archive.org/web/19991010131715/http://www.owlnet.rice.edu/~elec539/Projects97/cult/node2.html, 2 pgs.
"Supersonic to feature Aixplorer Ultimate at ECR", AuntiMinnie.com, 3 pages (Feb. 2018).
Al Sallab et al., "Self Learning Machines Using Deep Networks", Soft Computing and Pattern Recognition (SoCPaR), 2011 Int'l. Conference of IEEE, Oct. 14, 2011, pp. 21-26.
Berg, WA et al., "Combined screening with ultrasound and mammography vs mammography alone in women at elevated risk of breast cancer", JAMA 299:2151-2163, 2008.
Burbank, Fred, "Stereotactic Breast Biopsy: Its History, Its Present, and Its Future", published in 1996 at the Southeastern Surgical Congress, 24 pages.
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Caroline, B.E et al., "Computer aided detection of masses in digital breast tomosynthesis: A review", 2012 International Conference on Emerging Trends in Science, Engineering and Technology (INCOSET), Tiruchirappalli, 2012, pp. 186-191.
Carton, AK, et al., "Dual-energy contrast-enhanced digital breast tomosynthesis—a feasibility study", BR J Radiol. Apr. 2010;83 (988):344-50.
Chan, Heang-Ping et al., "Computer-aided detection system for breast masses on digital tomosynthesis mammograms: Preliminary Experience", Radiology, Dec. 2005, 1075-1080.
Chan, Heang-Ping et al., "ROC Study of the effect of stereoscopic imaging on assessment of breast lesions," Medical Physics, vol. 32, No. 4, Apr. 2005, 1001-1009.
Chen, SC, et al., "Initial clinical experience with contrast-enhanced digital breast tomosynthesis", Acad Radio. Feb. 2007 14(2):229-38.
Cho, N. et al., "Distinguishing Benign from Malignant Masses at Breast US: Combined US Elastography and Color Doppler US-Influence on Radiologist Accuracy", Radiology, 262(1): 80-90 (Jan. 2012).
Conner, Peter, "Breast Response to Menopausal Hormone Therapy—Aspects on Proliferation, apoptosis and Mammographic Density", 2007 Annals of Medicine, 39;1, 28-41.
Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.
Diekmann, Felix., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain, C., et al., "Contrast-enhanced digital mammography", Eur J Radiol. 2009; 69:34-42.
Dromain, Clarisse et al., "Dual-energy contrast-enhanced digital mammography: initial clinical results", European Radiology, Sep. 14, 2010, vol. 21, pp. 565-574.
Dromain, Clarisse, et al., "Evaluation of tumor angiogenesis of breast carcinoma using contrast-enhanced digital mammography", AJR: 187, Nov. 2006, 16 pages.
Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.
E. Shaw de Paredes et al., "Interventional Breast Procedure", published Sep./Oct. 1998 in Curr Probl Diagn Radiol, pp. 138-184.
EFilm Mobile HD by Merge Healthcare, web site: http://itunes.apple.com/bw/app/efilm-mobile-hd/id405261243?mt=8, accessed on Nov. 3, 2011 (2 pages).
EFilm Solutions, eFilm Workstation (tm) 3.4, website: http://estore.merge.com/na/estore/content.aspx?productID=405, accessed on Nov. 3, 2011 (2 pages).
Elbakri, Idris A. et al., "Automatic exposure control for a slot scanning full field digital mammography system", Med. Phys. Sep. 2005; 32(9):2763-2770, Abstract only.
Ertas, M. et al., "2D versus 3D total variation minimization in digital breast tomosynthesis", 2015 IEEE International Conference on Imaging Systems and Techniques (IST), Macau, 2015, pp. 1-4.
Feng, Steve Si Jia, et al., "Clinical digital breast tomosynthesis system: Dosimetric Characterization", Radiology, Apr. 2012, 263(1); pp. 35-42.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Freiherr, G., "Breast tomosynthesis trials show promise", Diagnostic Imaging—San Francisco 2005, V27; N4:42-48.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Ghiassi, M. et al., "A Dynamic Architecture for Artificial Networks", Neurocomputing, vol. 63, Aug. 20, 2004, pp. 397-413.
Giger et al. "Development of a smart workstation for use in mammography", in Proceedings of SPIE, vol. 1445 (1991), pp. 101103; 4 pages.
Giger et al., "An Intelligent Workstation for Computer-aided Diagnosis", in RadioGraphics, May 1993, 13:3 pp. 647-656; 10 pages.
Glick, Stephen J., "Breast CT", Annual Rev. Biomed. Eng., 2007, 9;501-26.
Green, C. et al., "Deformable mapping using biochemical models to relate corresponding lesions in digital breast tomosynthesis and automated breast ultrasound images", Medical Image Analysis, 60: 1-18 (Nov. 2019).
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Ijaz, Umer Zeeshan, et al., "Mammography phantom studies using 3D electrical impedance tomography with numerical forward solver", Frontiers in the Convergence of Bioscience and Information Technologies 2007, 379-383.
Jochelson, M., et al., "Bilateral Dual Energy contrast-enhanced digital mammography: Initial Experience", RSNA 2010, 96th Scientific Assembly and Scientific Meeting, 2 pages.
Jong, RA, et al., Contrast-enhanced digital mammography: initial clinical experience. Radiology 2003; 228:842-850.
Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.
Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.

(56) References Cited

OTHER PUBLICATIONS

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Kopans, Daniel B., "Breast Imaging", 3rd Edition, Lippincott Williams and Wilkins, published Nov. 2, 2006, pp. 960-967.
Kopans, et. al. Will tomosynthesis replace conventional mammography? Plenary Session SFN08: RSNA 2005.
Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).
Lehman, CD, et al. MRI evaluation of the contralateral breast in women with recently diagnosed breast cancer. N Engl J Med 2007; 356:1295-1303.
Lewin,JM, et al., Dual-energy contrast-enhanced digital subtraction mammography: feasibility. Radiology 2003; 229:261-268.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.
Lindfors, KK, et al., Dedicated breast CT: initial clinical experience. Radiology 2008; 246(3): 725-733.
Love, Susan M., et al. "Anatomy of the nipple and breast ducts revisited", Cancer, American Cancer Society, Philadelphia, PA, vol. 101, No. 9, Sep. 20, 2004, pp. 1947-1957.
Mahesh, Mahadevappa, "AAPM/RSNA Physics Tutorial for Residents—Digital Mammography: An Overview", Nov.-Dec. 2004, vol. 24, No. 6, 1747-1760.
Metheany, Kathrine G et al., "Characterizing anatomical variability in breast CT images", Oct. 2008, Med. Phys. 35 (10); 4685-4694.
Niklason, L., et al., Digital tomosynthesis in breast imaging. Radiology. Nov. 1997; 205(2):399-406.
Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
Pediconi, "Color-coded automated signal intensity-curve for detection and characterization of breast lesions: Preliminary evaluation of new software for MR-based breast imaging," International Congress Series 1281 (2005) 1081-1086.
Poplack, SP, et al, Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results". . . presented at 2007 Radiological Society of North America meeting, Chicago IL.
Reynolds, April, "Stereotactic Breast Biopsy: A Review", Radiologic Technology, vol. 80, No. 5, Jun. 1, 2009, pp. 447M-464M, XP055790574.
Bakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.
Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.
Sechopoulos, et al., "Glandular radiation dose in tomosynthesis of the breast using tungsten targets", Journal of Applied Clinical Medical Physics, vol. 8, No. 4, Fall 2008, 161-171.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Taghibakhsh, f. et al., "High dynamic range 2-TFT amplified pixel sensor architecture for digital mammography tomosynthesis", IET Circuits Devices Syst., 2007, 1(10, pp. 87-92.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Varjonen, Mari, "Three-Dimensional Digital Breast Tomosynthesis in the Early Diagnosis and Detection of Breast Cancer", IWDM 2006, LNCS 4046, 152-159.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", AM J Clin Pathol. Nov. 2004 122(5):696-703.
Wen, Junhai et al., "A study on truncated cone-beam sampling strategies for 3D mammography", 2004, IEEE, 3200-3204.
Williams, Mark B et al., "Optimization of exposure parameters in full field digital mammography", Medical Physics 35, 2414 (May 20, 2008); doi: 10.1118/1.2912177, pp. 2414-2423.
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Yin, H.M., et al., "Image Parser: a tool for finite element generation from three-dimensional medical images", BioMedical Engineering Online. 3:31, pp. 1-9, Oct. 1, 2004.
Zhang, Yiheng et al., "A comparative study of limited-angle cone-beam reconstruction methods for breast tomosynthesis", Med Phys., Oct. 2006, 33(10): 3781-3795.
Zhao, Bo, et al., "Imaging performance of an amorphous selenium digital mammography detector in a breast tomosynthesis system", May 2008, Med. Phys 35(5); 1978-1987.
Perek, S. et al., "Siamese network for dual-view mammography mass matching", Image Analysis for Moving Organ, Breast & Thoracic Images: 3rd Int'l Workshop, RAMBO 2018, 4th Int'l Workshop, BIA 2018, and 1st Int'l Workshop, TIA 2018, Proceedings 3. Springer International Publishing, 2018.

* cited by examiner

NEEDLE BREAST BIOPSY SYSTEM AND METHOD OF USE

RELATED APPLICATIONS

This application is a continuation of U.S. patent application Ser. No. 18/107,113, filed Feb. 8, 2023, now U.S. Pat. No. 12,193,886, which is a continuation of U.S. patent application Ser. No. 16/809,355, filed Mar. 4, 2020, now U.S. Pat. No. 11,701,199, which is a continuation of U.S. patent application Ser. No. 12/715,591, filed Mar. 2, 2010, now U.S. Pat. No. 10,595,954, which claims the benefit of U.S. Provisional Patent Application No. 61/249,772, filed Oct. 8, 2009, the entire disclosures of which are incorporated herein by reference in their entireties. To the extent appropriate, a claim of priority is made to each of the above disclosed applications.

BACKGROUND OF THE INVENTION

Mammography is a well-established method of breast imaging which may be used for breast cancer screening and diagnosis. Screening mammograms are preferably obtained annually for female members of the population over the age of forty, or those having a genetic risk of breast cancer. Should masses or calcifications ('regions of interest') be identified during a screening mammogram, the patient may require further diagnosis. Such diagnosis may involve biopsying the region of interest and analyzing excised tissue.

Various imaging modalities have historically been used during breast biopsies. The imaging modalities include ultrasound imaging, x-ray imaging and magnetic resonance imaging. Performing a breast biopsy typically involves positioning the patient, visualizing the region of interest using the imaging equipment, targeting coordinates of the region and retrieving cells or tissue from the targeted region. Cells or tissue may be retrieved in a variety of ways, including through open surgery, fine needle aspiration, core needle biopsy or vacuum assisted biopsy. Open surgery, the most invasive procedure, is generally performed by a radiologist placing a wire into the breast during visualization of the region of interest, where the wire extends into the region that is to be excised. The patient is then transferred to surgery and tissue is retrieved using the wire to locate the region of interest.

Fine needle aspiration, core needle biopsies and vacuum assisted biopsies are less invasive than open surgery, allowing cells and tissue to be obtained without the need for open surgery. All are needle biopsies, with the size of the needle, and thus the corresponding size (and number) of the biopsied samples, being differentiators. In each procedure the patient is positioned, the region of interest is visualized, the needle of the biopsy device is advanced to the target region of interest and the tissue is retrieved. Fine needle aspiration and core needle biopsy devices typically retrieve one tissue sample and their advancement to the target may be monitored using an imaging modality such as ultrasound. Vacuum assisted biopsy devices generally have larger needles and can extract multiple cores.

X-ray imaging in stereotactic mode is generally used for breast biopsies because it is desirable to visualize and target regions in a three dimensional volume. Stereotactic biopsies obtain volume information using x-ray images taken in at least two planes. The x-ray images are then processed to localize a target region of interest in three-dimensional space using the principal of parallax to determine the depth, or Z dimension, of the target region.

U.S. Patent Application 2008/0045833, filed Feb. 21, 2008 and incorporated herein by reference, describes systems and methods for using tomosynthesis for lesion localization during breast biopsy. Tomosynthesis (tomo) is a method of performing three dimensional (3D) breast x-ray imaging. It generates images of cross sectional slices through a compressed breast, and also is used to identify breast pathologies. One of the advantages of tomosynthesis is that the images are three-dimensional so that once an area of interest is identified in an image its exact 3D coordinate in the breast can be calculated or estimated, e.g. from the x, y coordinate in the image of a slice and from the z, or depth, coordinate given by the image slice depth location. Another advantage of tomosynthesis is its ability to provide high contrast visibility of objects by the suppression of images from objects at different heights in the breast. Because of its superior contrast visibility, it is expected that there will be pathologies seen on the tomo images that will not be visible using standard x-ray mammography, stereotactic devices, ultrasound or even MRI. For this reason, it is desired to develop localization methods using tomosynthesis systems that utilize tomosynthesis' natural 3D localization abilities.

SUMMARY OF THE INVENTION

According to one aspect of the invention a stereotactic needle biopsy assembly is provided for mounting between an x-ray source and a detector of an x-ray imaging system. The stereotactic assembly includes a mounting arm for supporting a biopsy device at an angle offset from normal to a plane of defined by the detector. In some embodiments, the assembly may also include a lateral side arm permitting lateral access to the breast. The stereotactic needle biopsy assembly includes a guidance module for motorized guidance of the biopsy device to a target location during a biopsy for excising tissue. Because the biopsy needle is angled relative to the detector, x-ray imaging may be performed during the biopsy procedure without interference by the biopsy device. In addition the angled biopsy needle allows improved access to the axilla and chest wall of the patient.

In one embodiment the needle biopsy assembly includes a motor or equivalent mechanism enabling automatic advancement of the biopsy device towards an identified biopsy target location. The system advantageously additionally includes mechanisms enabling manual advancement of the device. The system permits the user to define stop locations along the biopsy path to the target, for transitioning between automated and manual control.

In one embodiment the needle biopsy assembly may include a control module, mounted on the needle biopsy assembly, the control module enabling the medical personnel to control the automated movement of the device towards the target without leaving the patient. The control module in some embodiments may display information related to the biopsy procedure, such as the relative locations of the needle and the target. The control module may also provide visible or audible warnings to the user, for example to warn of proximity of the needle to the chest wall, the breast platform, or other undesirable position. In one embodiment the control buttons of the control module are arranged to preclude unintended advancement of the biopsy device.

The stereotactic biopsy device of the present invention may be coupled to any x-ray system, whether upright or prone, including but not limited to mammography systems, tomosynthesis systems, and combination mammography/ tomosynthesis systems. The system flexibly supports the use of any mode of image capture (i.e., scout, two dimensional mammogram, three-dimensional reconstructed volume) and any combination of two dimensional or three dimensional image data for either or both target visualization and target localization. With such an arrangement, a needle biopsy assembly having improved patient coverage is provided for use with a variety of different x-ray imaging platforms.

In particular such an assembly may easily be integrated into a tomosynthesis imaging system. Such a tomosynthesis system could be readily adapted to provide automated stereotactic image capture for use with the needle biopsy assembly by capturing tomo projection images at desired stereotactic angles. Such a system has the added advantage of reducing patient exposure because tomosynthesis projection images are generally obtained at lower dose than conventional mammograms and therefore stereotactic volume information (for use in visualization or targeting) can be obtained at reduced dosage. These and other advantages will be described in further detail below.

DETAILED DESCRIPTION

Figure 1:
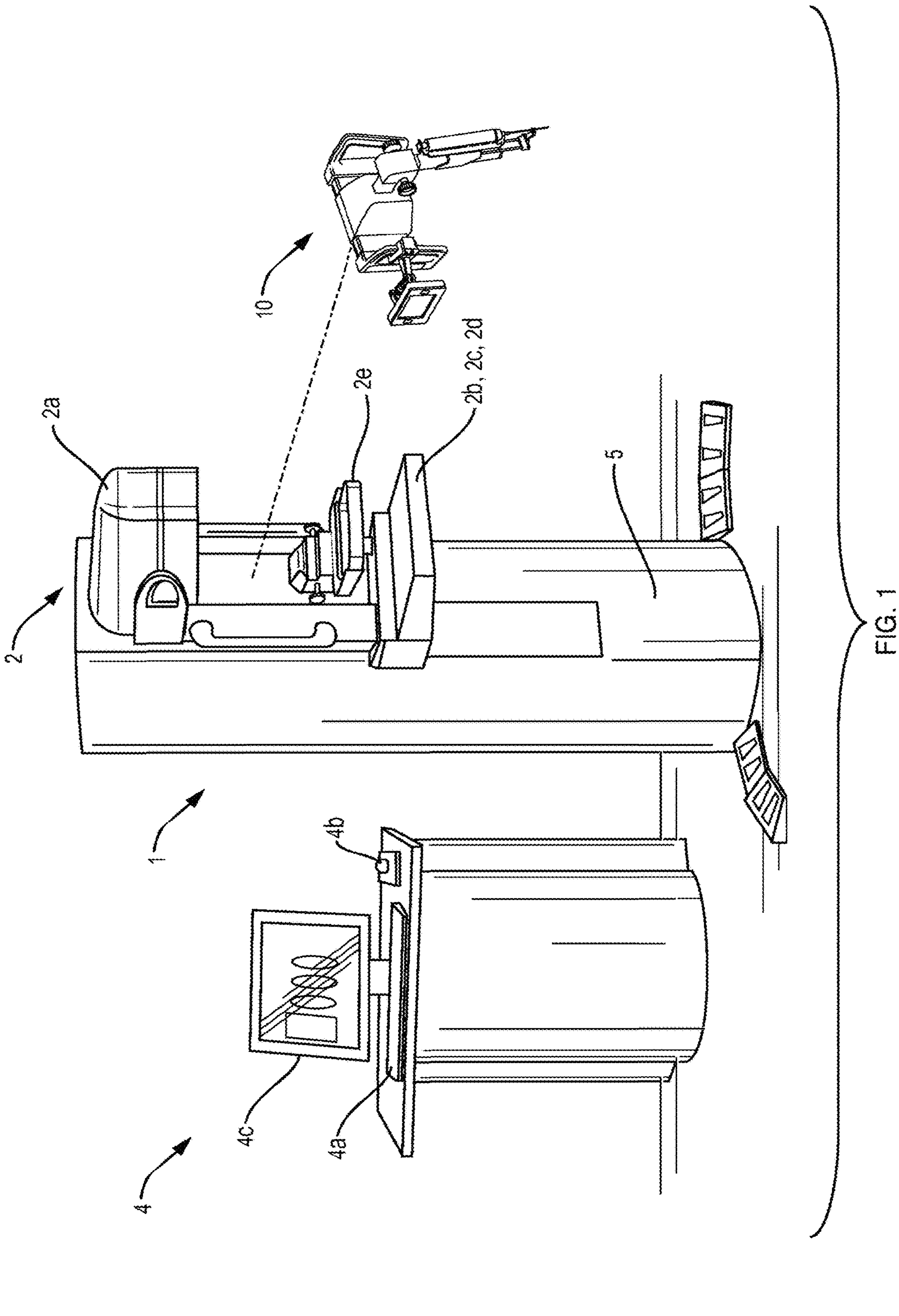
FIG. 1 illustrates an x-ray imaging system which may advantageously incorporate the needle biopsy assembly of the present invention.

Breast tomosynthesis systems generally include an x-ray source mounted on a rotatable arm of a gantry and an x-ray detector positioned generally normal to the x-ray source when the x-ray source is at zero position. During tomosynthesis image acquisition, the x-ray source is rotated over a limited angular range. At various points in the x-ray source trajectory the source is activated and an image is captured by the detector. Each image captured at each point is referred to as a projection image. Computer programs are used to reconstruct a three dimensional volume from the projection images and the three dimensional volume is used for lesion detection. One example of an x-ray imaging system capable of mammographic and tomosynthesis imaging and which may be adapted to incorporate the present invention is shown in FIG. 1.

The mammography/tomosynthesis system is shown to include an acquisition work station (AWS) 4 and gantry 1 supporting an x-ray imaging assembly 2. Such a mammography/tomosynthesis system is currently available from the common assignee under the trade name Selenia Dimensions, and is representative of merely one x-ray system on which the needle biopsy assembly 10 of the present invention may be mounted. The gantry 1 supports a C-arm that can move up or down along the gantry to a selected height, driven by motor(s) controlled by a health professional operating the system. C-arm carries an x-ray tube 2*a* at an upper end and a breast tray 2*b* at a lower end. Tray 2*b* covers a flat panel x-ray image receptor 2*c*, spaced from the tray by a focused anti-scatter grid 2*d* (which may be retractable so that it can be removed from the space between tray 2*b* and receptor 2*c*). The C-arm also carries a compression paddle 2*e* that is between source 2*a* and breast tray 2*b* and is motorized to move away from tray 2*b* so a patient's breast can fit between tray 2*b* and paddle 2*e*, and closer to tray 2*b* so the patient's breast can be compressed and immobilized. The movement of paddle 2*e* is motorized and controlled by the health professional. Paddles 2*e* of different size and different configurations can be fitted on the gantry to suit different breast sizes or to suit imaging needs (i.e., for screening or diagnosis). In addition, the health professional can move paddle 2*e* along the width of tray 2*b* to a position in which paddle 2*e* matches the position of a breast that is not centered on tray 2*b*, as in the Selenia system currently offered by the common assignee. The system further includes other components, such as a control station 4 comprising interface devices such a keyboard 4*a* and trackball 4*b*, a display screen 4*c*, and control and image processing facilities.

According to one aspect of the invention a needle biopsy assembly 10 may easily be mounted in between the x-ray source and the x-ray detector of the imaging system 2. Unlike previous needle biopsy assemblies, the needle biopsy assembly of the present invention utilizes all of the existing components of the x-ray system, including the compression device and the x-ray detector. As a result, it can be appreciated that the needle biopsy assembly is a low cost solution which makes upright needle biopsy capability available to a variety of current x-ray imaging platforms.

Figure 2:
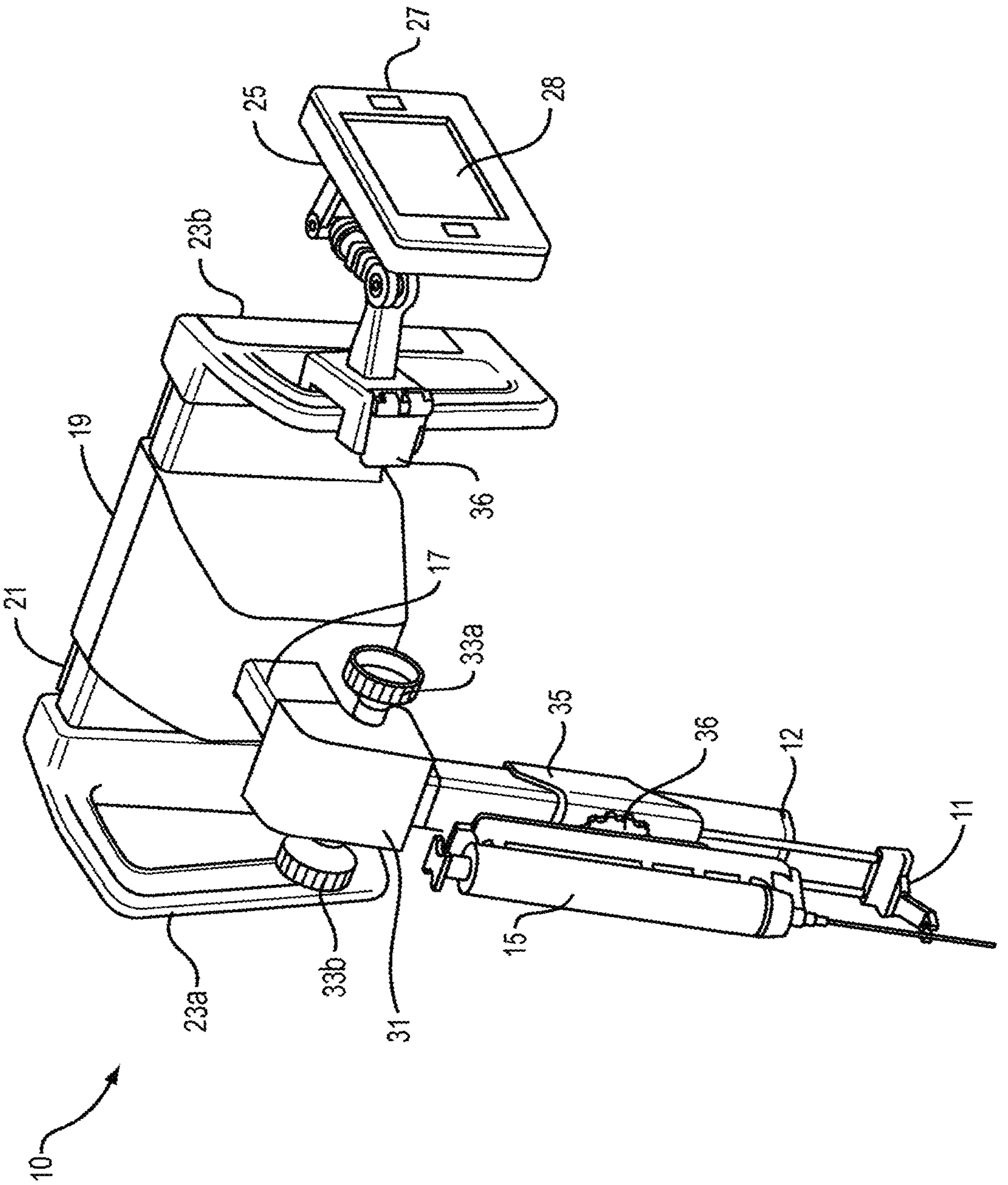
FIG. 2 illustrates one embodiment of the needle biopsy assembly of the present invention with a mounted biopsy device.

FIG. 2 illustrates the needle biopsy assembly 10 in more detail. Support bracket 21 extends between handles 23*a* and 23*b*, which facilitate transport of the assembly. Guidance module 19, mounted on support bracket 21, includes components for controlling the movement of the biopsy device 15. The biopsy device may be, for example, an Eviva™ vacuum assisted biopsy device manufactured and sold by Hologic, Inc. Fixed support arm 17 extends from the guidance module to connector 31. In one embodiment connector 31 connects angular support arm 12 to the fixed support arm 17 at a fixed angle. Alternative embodiments which include adjustment mechanisms for varying the angle of displacement between the angular support arm and the fixed support arm may be substituted herein as equivalents. Holster mount 35 is moveably coupled to the support arm. The linear movement may be mechanically controlled (i.e., via the guidance module and associated motors) and/or may be manually controlled using either or both of the thumbwheel knobs 33*a* and 33*b*. The holster mount 35 includes an attachment mechanism 36 that is adapted to receive biopsy holster 13. The biopsy device 15 sits within the biopsy holster 13. A needle support 11 may advantageously be coupled to the holster mount for needle stabilization. A control module 25 may be mounted to either of the handles, 23*b* or 23*a* via clamp 36. In various embodiments, each handle may include one or more electrical connectors which enable communication between the clamped control module 25 and the guidance module 19, and the medical professional may move the control module to either handle as a matter of preference. The control module 25 includes a user interface that enables a medical professional to control the biopsy procedure without the need to leave the patient. The control module includes a display 28 for displaying a status or other information about the biopsy, and one or more buttons 27 for controlling the movement of the biopsy device during the procedure.

Figure 3A:
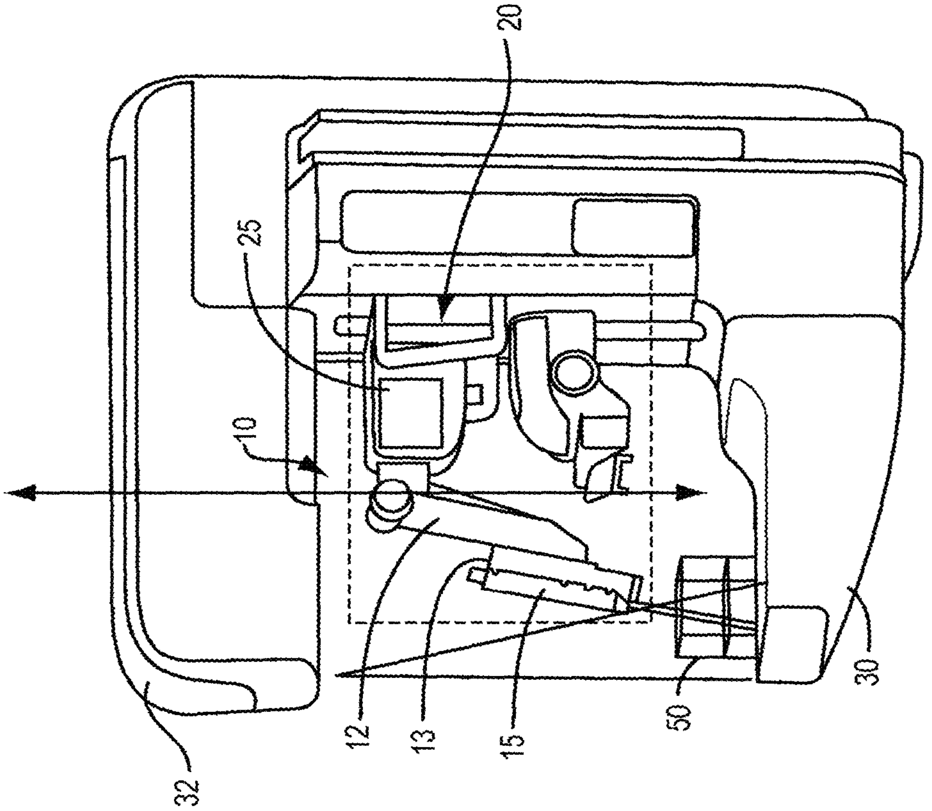
FIGS. 3A and 3B illustrates a portion of an x-ray system on which the needle biopsy assembly of the present invention is mounted and is used to illustrate how the angular tilt of the biopsy device reduces interference during x-ray imaging.
Figure 3B:
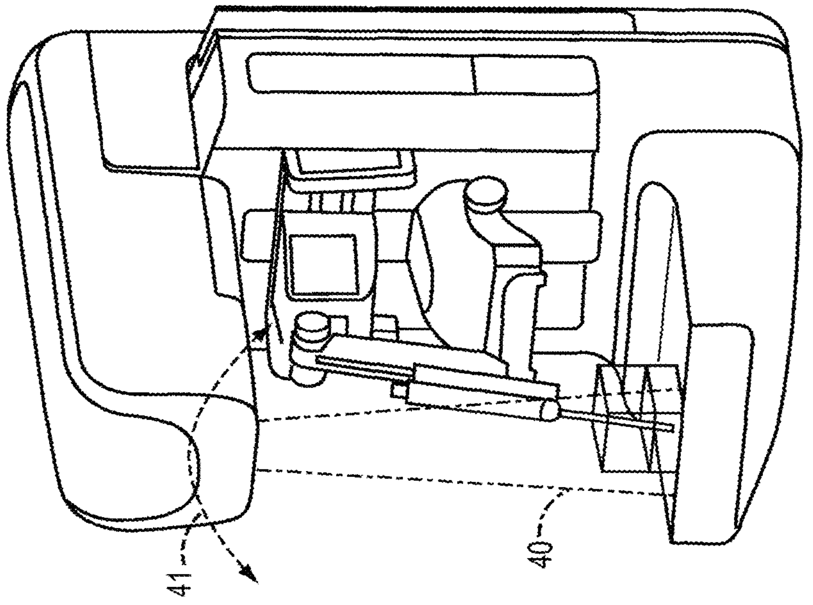

FIGS. 3A and 3B illustrate the needle biopsy assembly 10 mounted on a gantry of an x-ray imaging system. Various embodiments of the needle biopsy assembly may be used with either an upright or prone imaging system, for the purposes of this application an embodiment for use with an upright breast tomosynthesis imaging system (such as the Dimensions™M Breast Tomosynthesis imaging system provided by Hologic, Inc.) is described. An exemplary tomosynthesis imaging system may include a tube head 32 supporting a cone beam or other x-ray source, and a compression platform 30 encasing an x-ray detector. The tube head 32 is rotatably mounted on a gantry (not shown) to enable the tube head to rotate in along an angular trajectory generally designated by the dashed line 41 in FIG. 3B.

In one embodiment the needle biopsy assembly 10 includes clamps, hooks or other attachment means for mounting the needle biopsy assembly to the gantry of the tomosynthesis imaging system. Advantageously the clamps are mated to features of the gantry that support other attached devices (such as face shields and the like) although such reuse is not a requirement.

In the example of FIGS. 3A and 3B, the holster 13 is coupled to the holster mount on the fixed angle arm 12, and the fixed angle arm 12 is fixedly mounted on the support arm 17 at an angle offset from normal by 10 degrees, although it is readily appreciated that the offset angle may vary and is largely a matter of design choice. Angling the arm 12 (and by consequence the biopsy device 15) allows the biopsy device to be advanced to a desired location within a biopsy target area (indicated generally by the target area 50) without the biopsy device and holster introducing artifacts into the x-ray image. As shown in FIG. 3B, the cone beam x-ray source will extend into the target area 50, but the device 15 does not fall within the cone beam. It should be noted that although a 10 degree fixed angle is disclosed, the present invention is not limited to any particular fixed angle and it is appreciated that the selected fixed angle may differ in response to particular geometries of the imaging systems and tissue removal tools. In a broadest sense, the present invention encompasses the idea of angling a biopsy needle to limit the introduction of visual artifacts caused by the needle during x-ray imaging.

Figure 4:
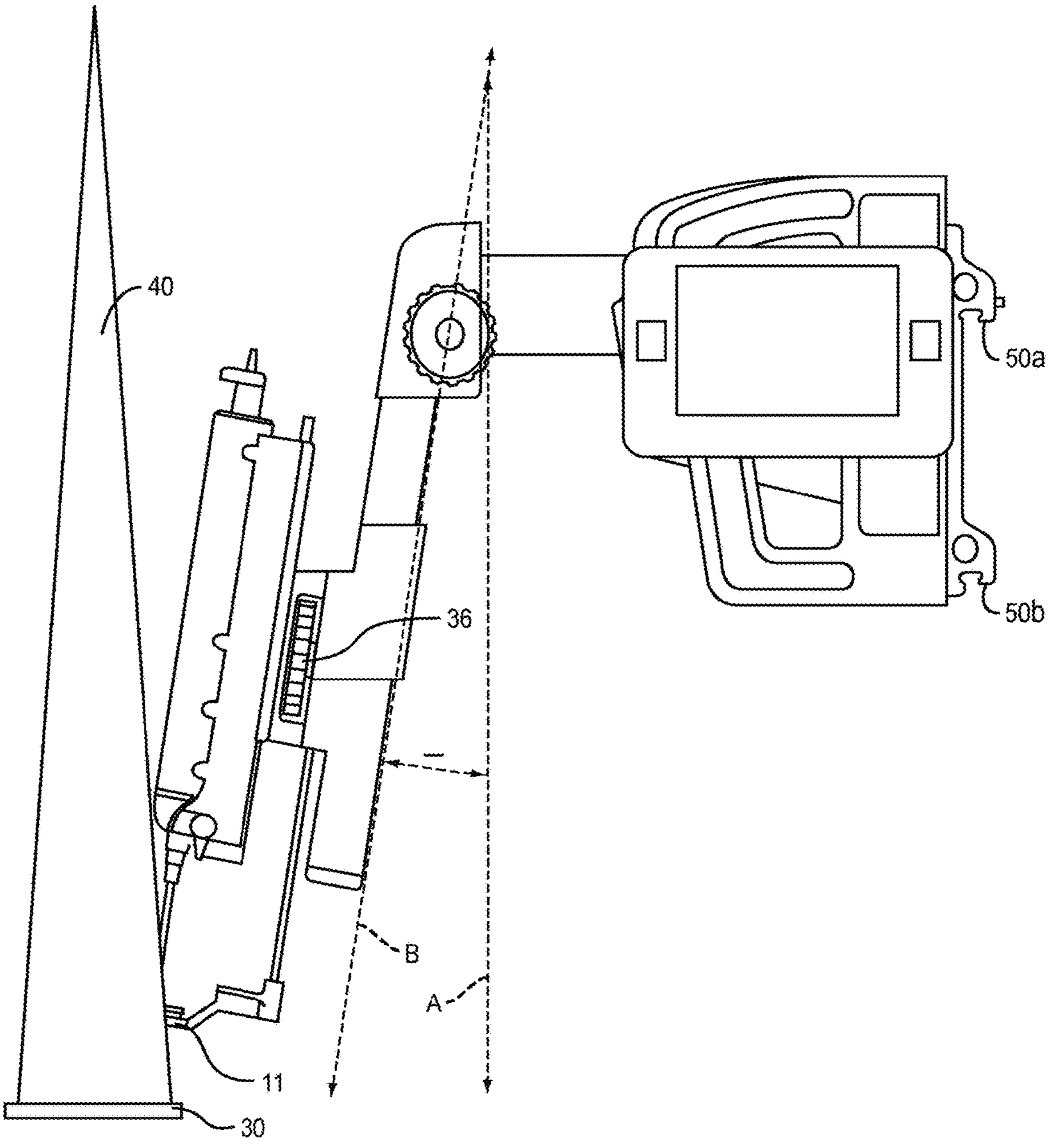
FIG. 4 is a side view of the needle biopsy assembly of the present invention, illustrating in more detail the angular tilt of the biopsy device support arm.

FIG. 4 is a side view of an exemplary embodiment of a needle biopsy assembly of the present invention. In FIG. 4, line A is within a plane that is ‘normal’ to the plane of the x-ray detector 30. Line B illustrates the angular displacement of the biopsy device, and therefore the device is offset from the normal by an angular measure of 0. As a result the biopsy device will interfere with biopsy imaging.

Also shown in more detail in FIG. 4 are exemplary coupling mechanisms S0*a* and sob of the needle biopsy assembly 10. The coupling mechanisms S0*a* and S0*b* are adapted to mate with complementary features of the gantry. Other types of coupling mechanisms, including latches, hooks, slots and the like may be readily substituted herein as equivalents.

Figure 5:
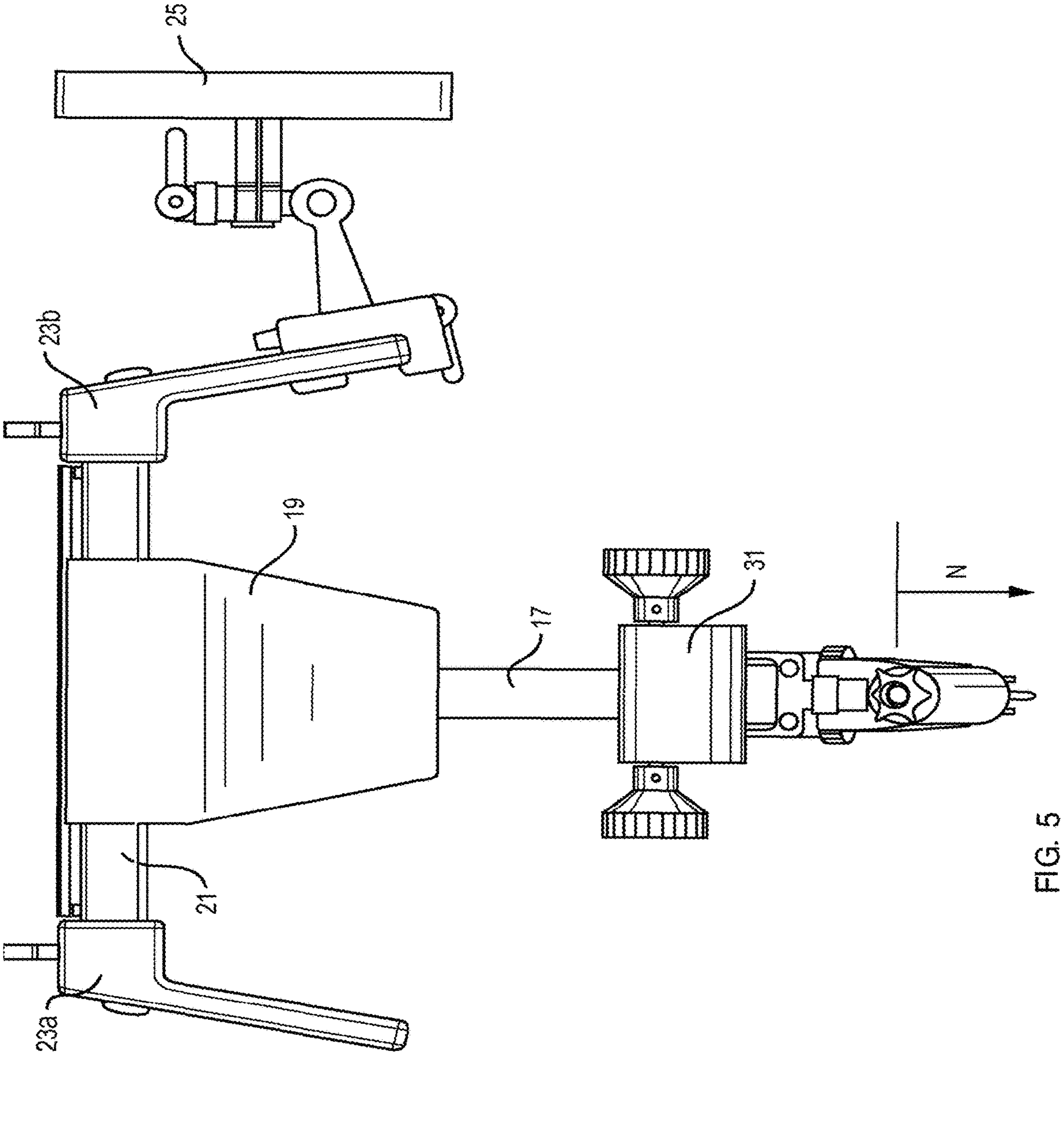
FIG. 5 is a top down view of the needle biopsy assembly of the present invention.

FIG. 5 is a top down view of the exemplary embodiment of the needle biopsy assembly, shown with only a subset of components labeled for case of reference. When viewing the needle biopsy assembly from this perspective, the displacement N of the needle tip which results from the angular tilt of the biopsy device is readily apparent. This view best illustrates the ability of this device to biopsy areas of the breast (such as the axilla tissue and tissue near the chest wall) which were previously difficult to access using prior art stereotactic devices.

Figure 6A:
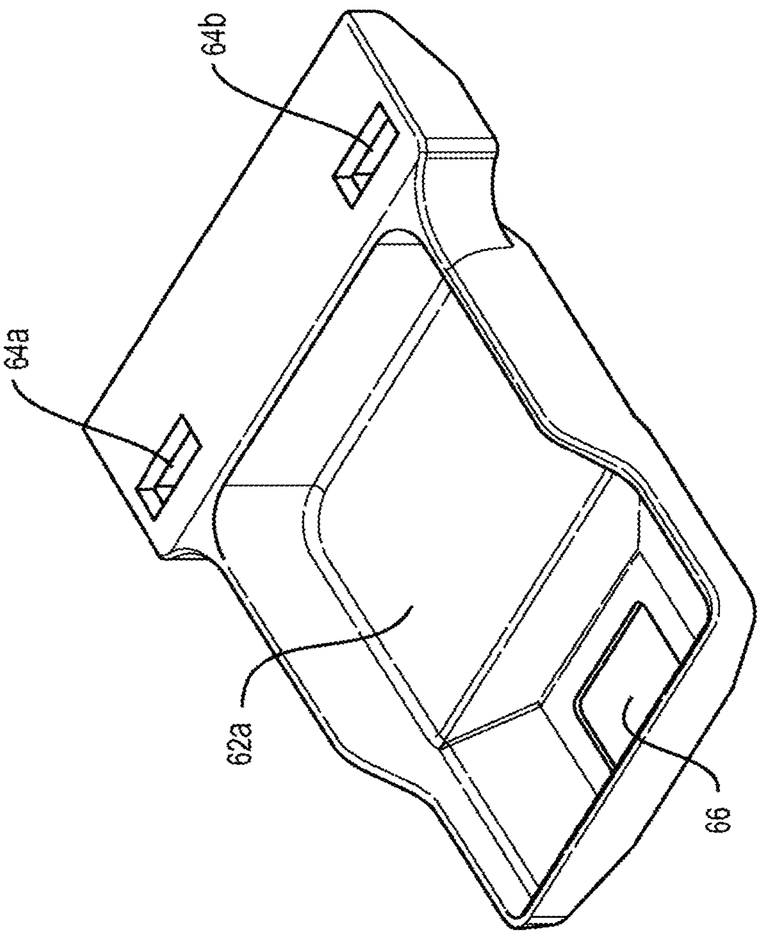
FIGS. 6A-6C illustrate compression paddles which may advantageously be used with the needle biopsy assembly of FIG. 2.
Figure 6C:
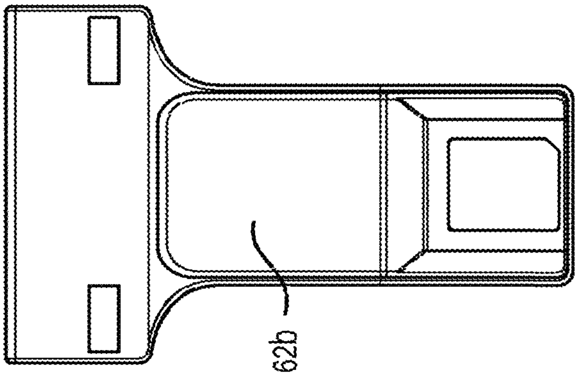
Figure 6B:
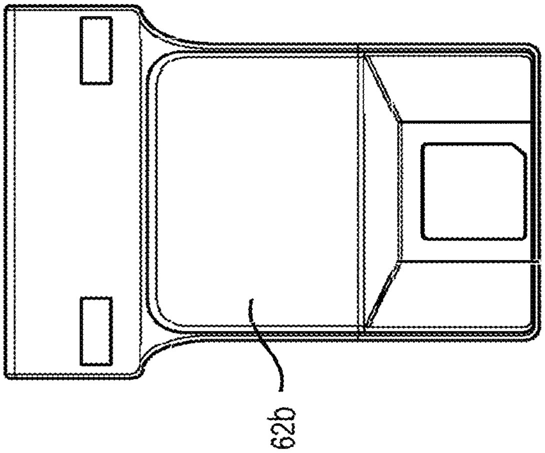
Figure 7:
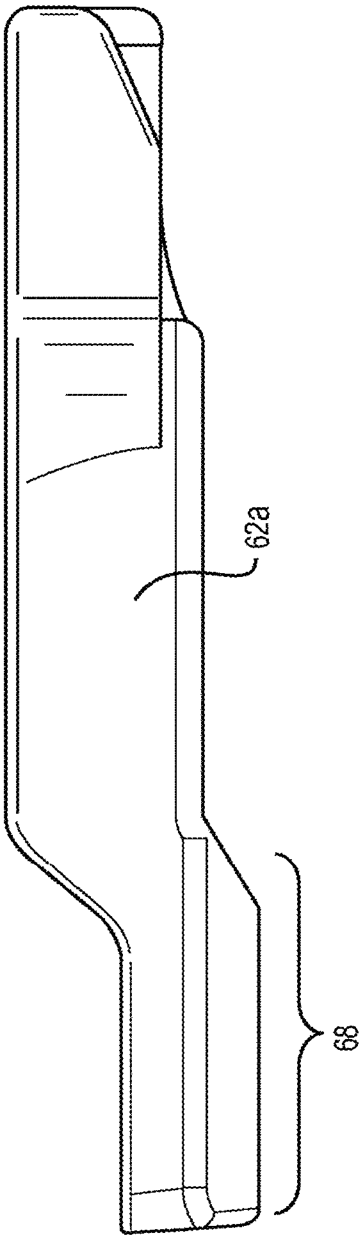
FIG. 7 is a side of a compression paddle which may be used with the needle biopsy assembly of the present invention.

FIGS. 6A through 6C illustrate various compression paddles which may be used with the present invention. In contrast to prior art needle biopsy compression paddles, which were generally fabricated of radio-opaque material having an opening therethrough for accepting the biopsy needle, the compression paddles 62A-62C are preferably radiolucent. Slots 64*a* and 64*b* are positioned to enable the compression paddle to be removably coupled to the compression device of the x-ray imaging system, allowing the paddles to easily be exchanged with the mammography/tomosynthesis paddles used for breast cancer screening. The biopsy compression paddles may be manufactured in different sizes to be used for different sized breasts, as shown in FIGS. 6B and 6C. An opening 66 is provided in each biopsy compression paddle. The opening enables the portion of the breast associated with the target to be exposed. As shown in FIG. 7, the portion 68 of the compression paddle 62*a* that surrounding the opening 66 is shaped to increase the compression on the portion of the breast being biopsied, thereby stabilizing the biopsied area.

One advantage of using the radiolucent breast compression paddle is that it allows full view of the detector; in prior art needle biopsy arrangement, only a portion of the detector associated with target localization was visible. This was sufficient because prior art biopsies were only performed on that portion of the tissue which was immediately below the opening in the compression paddle. However, the tilted needle of the present invention increases the amount of tissue that is available for biopsy beyond the border of the compression paddle opening-the needle in fact has the reach N shown in FIG. 5. Thus, as mentioned above, axilla tissue and tissue close to the chest wall can more readily be excised during biopsy.

Figure 8:
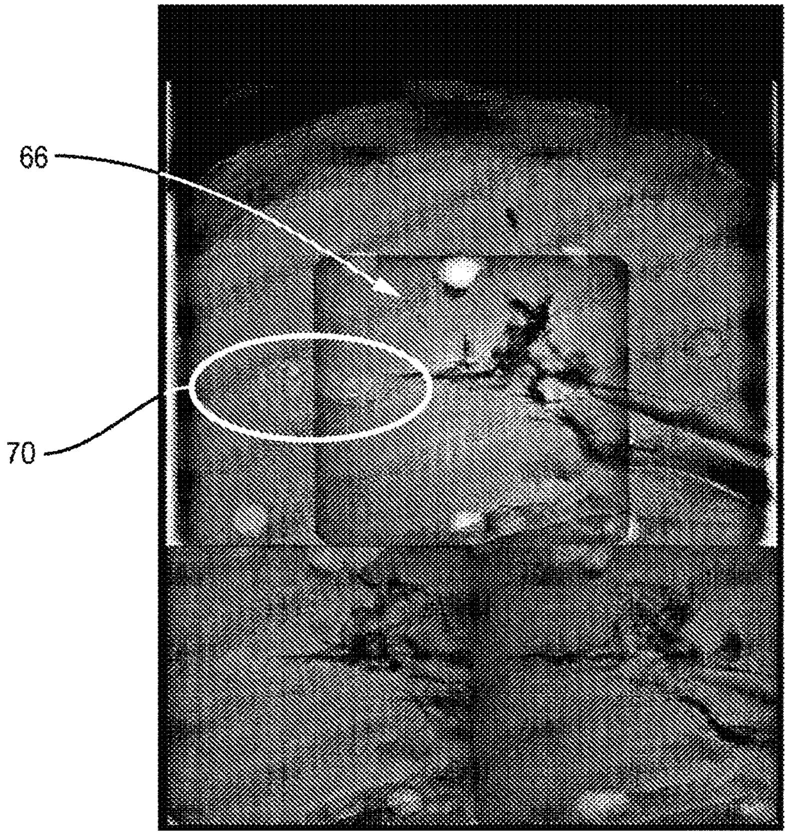
FIG. 8 illustrates an image capture at the acquisition workstation interface, wherein the entire detector is visible through the radiolucent compression paddle.

FIG. 8 illustrates a 20 image of a breast taken with a radiolucent biopsy paddle such as those shown in FIGS. 6 and 7. As shown in FIG. 8, one advantage of the radiolucent compression paddle is that the entire detector image may be viewed at the acquisition workstation interface; the radiologist is no longer limited in their access to information. As a result, the radiologist may see that portions of a lesion 80 extend beyond the compression paddle opening 66. This portion of the breast can be accessed using the tilted biopsy needle assembly of the present invention to ensure that all tissue is accessed for proper diagnosis.

Exemplary needle biopsy assemblies such as that described above may be generally used as follows. A patient who has been identified as a candidate for biopsy is positioned at the x-ray imaging system. At step 91 the biopsy compression paddle moves down towards the compression platform, compressing the patient's breast, and the process of visualizing the lesion is initiated at step 92. As mentioned briefly above, depending upon the capabilities of the x-ray imaging system, visualization of the lesion may be performed using a scout image, a mammogram, acquired stereotactic images, acquired tomosynthesis projection images, tomosynthesis reconstructed images, or any combination thereof. In one embodiment, an x-ray imaging system having tomosynthesis capabilities may be adapted to include a 'stereotactic mode', which, when selected, causes the x-ray imaging system to automatically retrieve the typical +/−15 degree stereotactic images and performs appropriate imaging processing on the stereotactic images to derive a stereotactic volume. One advantage of such an embodiment is that patient exposure may be reduced in tomosynthesis systems which use lower doses during projection image acquisition.

Once the lesion has been visualized, at step 93 the lesion is targeted. Targeting the lesion involves identifying the coordinates of the lesion using image data, and converting the coordinates from the Cartesian coordinate system of the images to the angular coordinate system of the tilted biopsy assembly using conversion techniques known to those of skill in the art. According to one aspect of the invention, different images, or combinations of images, may be used for visualizing the lesion than are used for targeting the lesion. For example, assume that a scout image is initially used to ensure that the patient is in position, and a pair of stereotactic images are used to visualize the lesion. If the lesion is found in the scout image, but not in both stereo images, the scout may be used in combination with the stereotactic image in which the lesion is located to derive target location information. Therefore, as above, depending upon the capabilities of the x-ray imaging system, the lesion target coordinates may be derived using a scout image, a mammogram, acquired stereotactic images, acquired tomosynthesis projection images, tomosynthesis reconstructed images, or any combination thereof.

Figure 10:
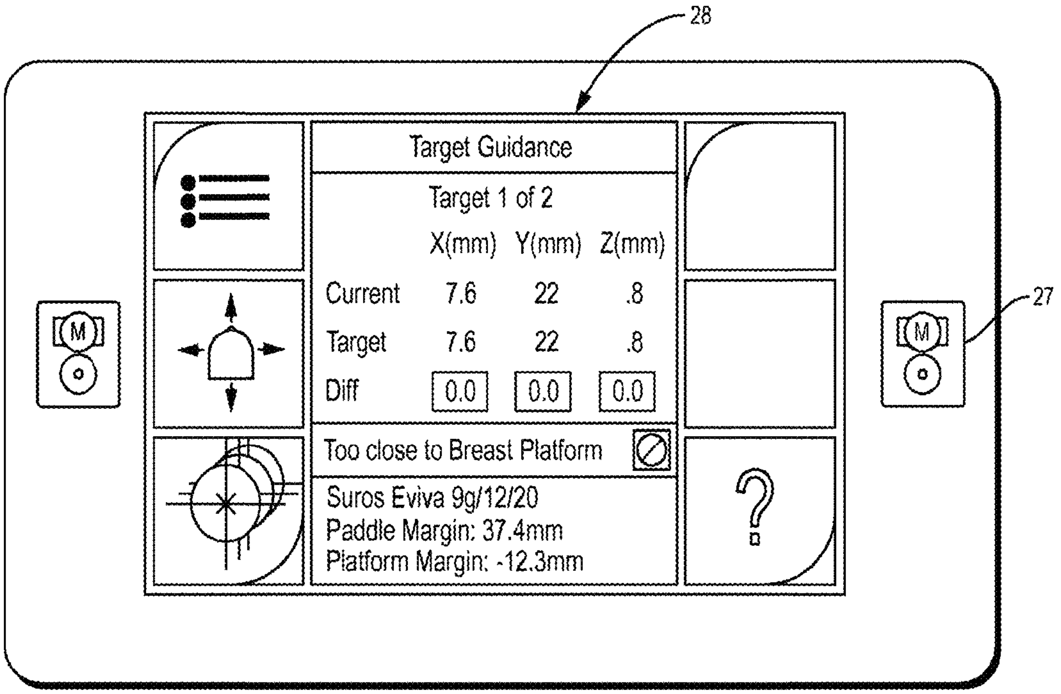
FIG. 10 illustrates an exemplary view of a user interface of the control unit of the needle biopsy assembly of FIG. 2.

At step 94, once the target coordinates are derived the medical professional can being the biopsy procedure by pressing control buttons required to move the biopsy needle. FIG. 10 illustrates an exemplary display and buttons of a control unit 25. The control unit includes a display 28 for displaying information related to the biopsy, such as information regarding needle size, distance to platform and paddle, needle coordinates, target coordinates, proximity to target and other related information. The control panel may also provide other helpful information to the user, such as warning indicators when the needle is too close to the breast platform, chest wall or skin line. As mentioned above, the warning indicators may be color coded or may provide other visual or audible indicators of undesirable conditions.

As mentioned above, in one embodiment the control unit also includes buttons (including button 27) positioned and arranged to allow single handed activation of the biopsy assembly while precluding accidental activation. In one embodiment, a pair of control buttons is provided, one on the front face of the control panel, and another on the back face of the control panel. Biopsy assembly movement may only be activated via simultaneous depression of both buttons. Other mechanisms for affirming operator intent may be substituted herein without affecting the scope of the invention.

According to one aspect of the invention, mechanical stops may be introduced into the biopsy path to stop automated needle movement at particular points along the path. For example, it may be desirable to switch to manual control of the needle movement, i.e., via knob 33*a* or 33*b* when the needle is within a desired range of the target. Or it may be desirable to provide a release brake for slow insertion of the needle into the breast. According to one embodiment, the number and location of mechanical stops is a programmable function which may be tailored to the individual preferences of a user of the system. Suffice it to say that numerous methods for mechanical advancement of the needle, including geared advancements, piston advancements, etc. are envisioned.

Figure 9:
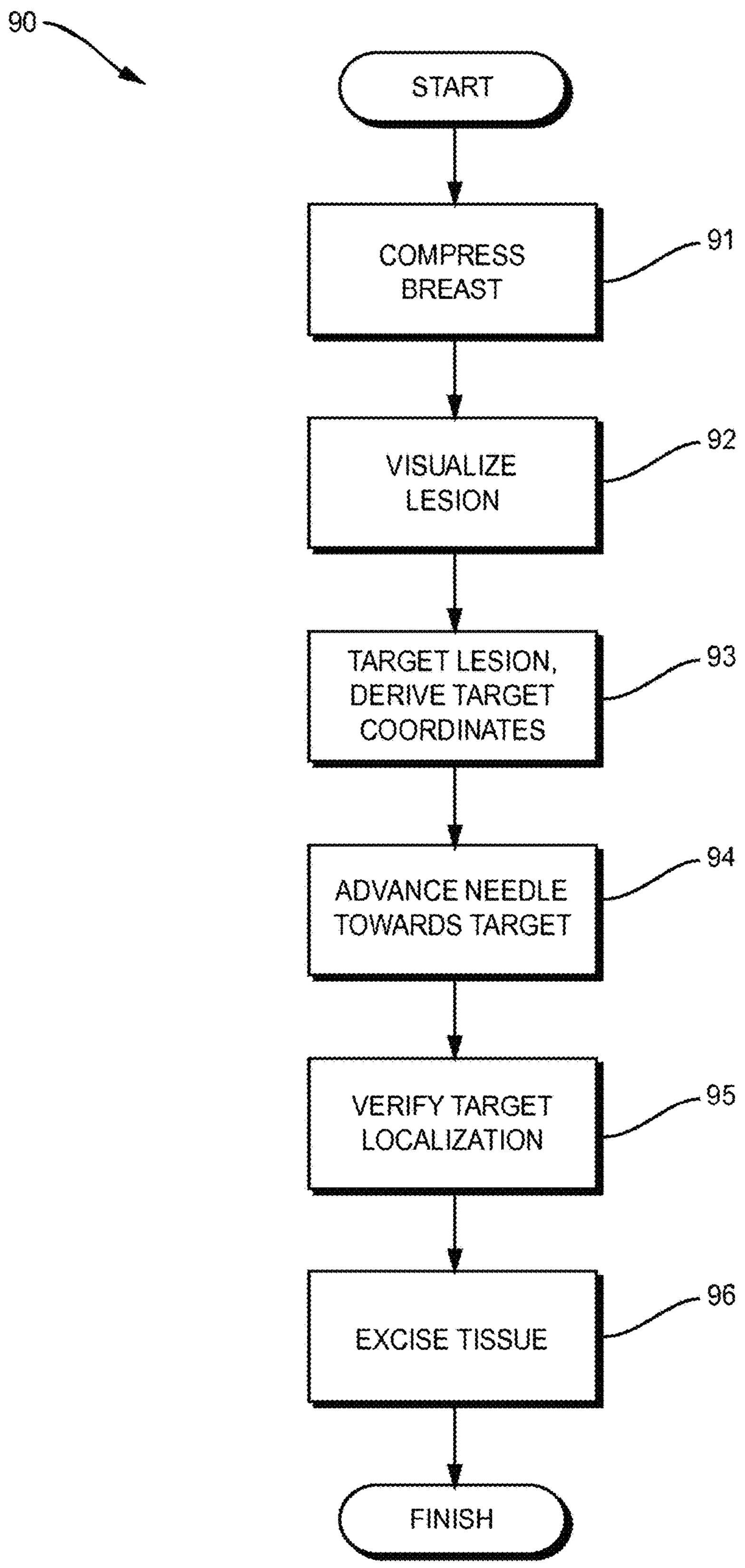
FIG. 9 is a flow diagram illustrating exemplary steps that may be performed during a biopsy using the needle biopsy assembly of the present invention.

Returning now to FIG. 9, at step 95 once the needle has been advanced to the target coordinates, an image may be acquired to verify that, in fact, the needle is positioned at the lesion. As the biopsy needle is out of the view of the x-ray imaging system such image may be obtained without interference. At step 96, when it is verified that the needle is at the target, the tissue may be excised, and the biopsy is complete. Although not explicitly shown in the flow diagram, steps 95 and 96 may be repeated to verify excision of the entire lesion.

Figure 11:
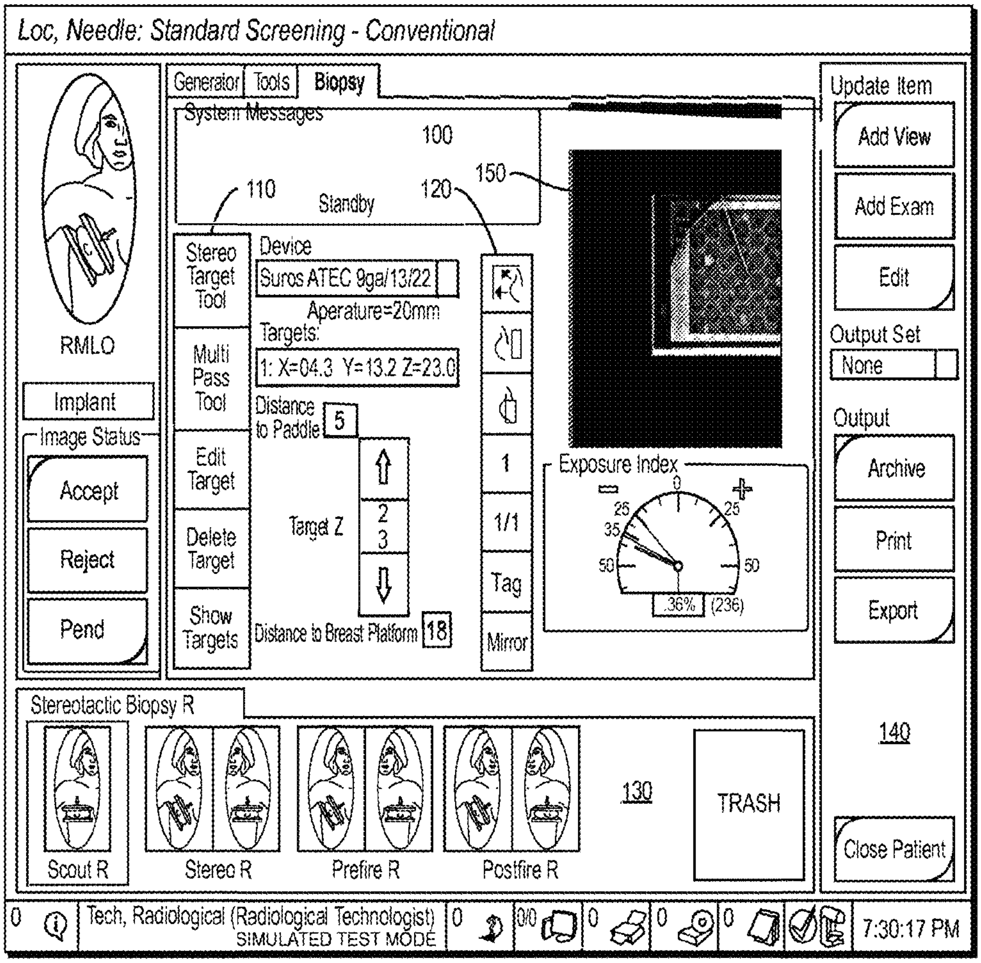
FIG. 11 illustrates an exemplary view of a user interface of an acquisition work station including functional modules and displays supporting and related to the needle biopsy assembly of FIG. 2.

Accordingly a biopsy needle assembly has been shown and described. According to another aspect of the invention, a user interface of the acquisition workstation is advantageously augmented with needle biopsy control capabilities. An example of user interface features that may be added to an acquisition workstation for use with the needle biopsy assembly is shown in FIG. 11. The user interface includes menus and/or control buttons or icons which enable the radiologist to control the display and output of information gathered during the biopsy. Targeting tools 110 allow the user to review, modify and delete target information. Image source selectors 120 (including stereotactic, tomosynthesis, scout, mammography, etc.) allow the radiologist to select which images to use for visualization or targeting. Image view selectors 130 allow the radiologist to quickly pull up and view any of the images that may have been acquired during the biopsy. Any of the images may be pulled up in the image window 150. Other information related to the biopsy, such as the type of biopsy device, the relative distances between the target and the compression plate/platform, etc., may also be included on the acquisition workstation. It should be noted that although a particular arrangement of buttons and icons has been shown in the representative view of FIG. 11, the present invention is not limited to any particular representation of such information, and other forms of pull down menus, hyperlinks, icons, buttons, and windows are considered equivalents hereto.

Figure 12A:
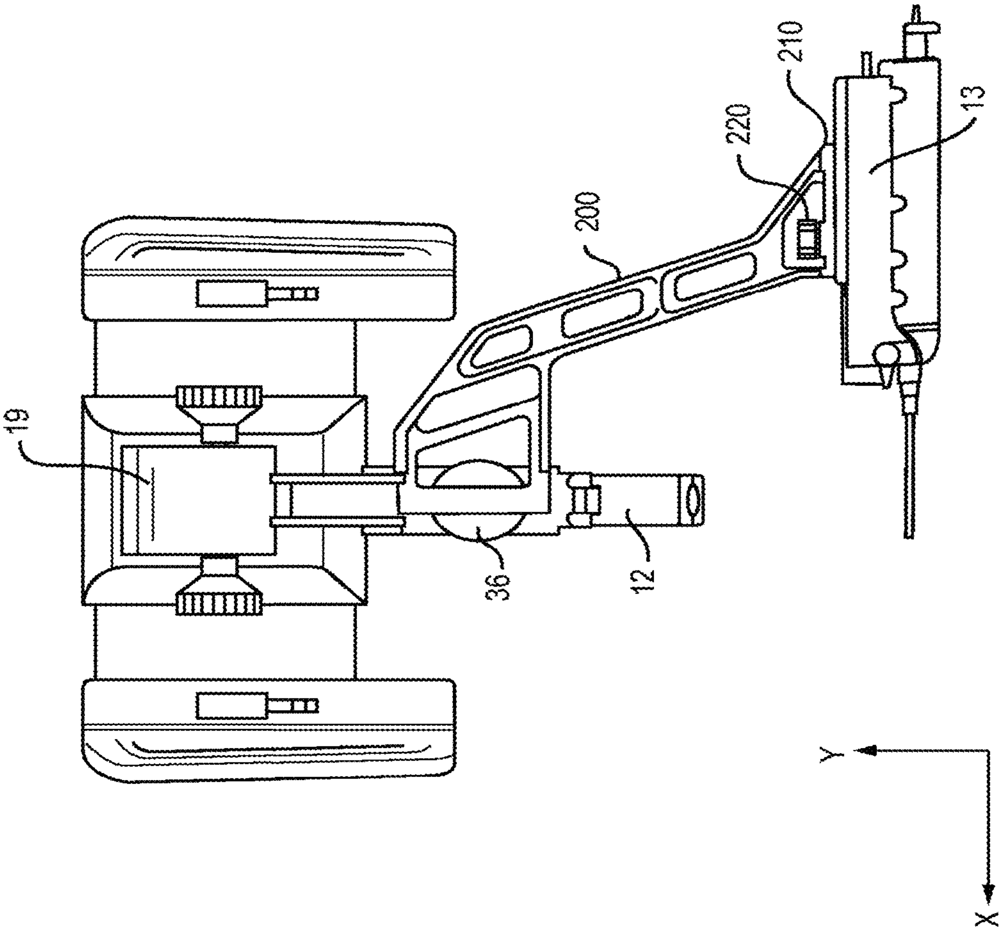
FIGS. 12A-12C illustrate views of an embodiment of the needle biopsy assembly with a lateral biopsy arm attachment.
Figure 12C:
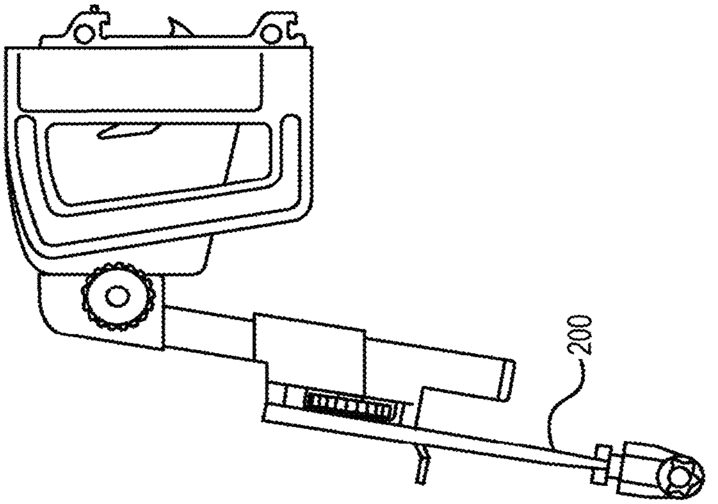
Figure 12B:
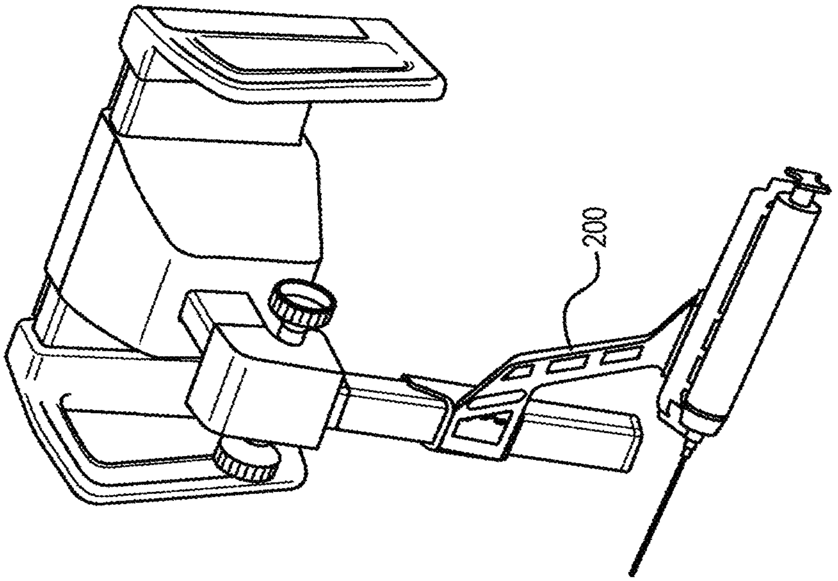

Although the above embodiments have described and illustrated a needle biopsy assembly for obtaining cores when the needle is positioned in a general cranial caudal orientation over the breast, according to one aspect of the invention lateral access to the breast may be achieved through the attachment of a lateral biopsy arm. The ability to perform lateral biopsies is particularly important for patients with thin breasts, as compression may reduce the thickness of the breast to such a degree that the tissue excision port at the distal tip of the biopsy needle cannot be fully inserted into the tissue. FIGS. 12A-12C illustrate various views of an embodiment of the needle biopsy assembly of the present invention that has been augmented with a lateral biopsy arm 200. FIG. 12A is a straight on view of the augmented assembly, FIG. 12B is a perspective view of the augmented assembly while FIG. 12C is a side view of the augmented assembly. The lateral biopsy arm supports the biopsy needle along a line substantially parallel to the detector, thereby permitting lateral excision of breast tissue. In the embodiment of FIGS. 12A-12C, the lateral biopsy arm includes a holster mount plate 210 and a thumb wheel 220. Rotation of the thumb wheel 220 results in manual translation of the needle in the direction indicated generally as X in FIG. 12A. Although manual translation in the X plane is shown, it is appreciated that motorized translation may be achieved by extending control from the guidance module 19 to the holster plate 210.

Targeting of the lesion, which defines how far the needle should move in the X, Y and Z direction is always done assuming that the needle is in a cranial-caudal orientation. According to one aspect of the invention, an electrical connection on the holster mount mounts with a connector on the lateral biopsy arm when the lateral biopsy arm is coupled to the holster mount 13 to enable the guidance module 19 to adjust the guidance coordinate system as appropriate for proper lesion localization.

Accordingly a tilted needle biopsy assembly having numerous advantages has been shown and described. Because the biopsy needle is angled relative to at least one of the detector and the x-ray source, x-ray imaging may be performed during the biopsy procedure without interference by the biopsy device. In addition the angled biopsy needle allows improved access to the axilla and chest wall of the patient. The stereotactic biopsy device of the present invention may be coupled to any x-ray system, whether upright or prone, including but not limited to mammography systems, tomosynthesis systems, and combination mammography/tomosynthesis systems. The system flexibly supports the use of any mode of image capture (i.e., scout, two dimensional mammogram, three-dimensional reconstructed volume) for either or both target visualization and target localization. With such an arrangement, a needle biopsy assembly having improved patient coverage is provided for use with a variety of different x-ray imaging platforms.

Having described exemplary embodiments, it can be appreciated that the examples described above are only illustrative and that other examples also are encompassed within the scope of the appended claims.

What we claim is:

1. An upright x-ray mammography imaging system comprising:

a gantry;

an x-ray tube rotatably supported on the gantry and configured to rotate relative to the gantry over an angular range;

a compression platform coupled to the gantry;

an x-ray receptor disposed within the compression platform, wherein the x-ray tube is configured to emit an x-ray and the x-ray receptor is configured to receive the emitted x-ray for generating x-ray image data, and wherein the x-ray receptor is positioned in a plane normal to the x-ray tube when the x-ray tube is at a zero position on the gantry;

a compression paddle releasably couplable onto the gantry and spaced apart from each of the x-ray tube and the compression platform, wherein the compression paddle and the compression platform are configured to compress a breast of a patient; and a biopsy guidance assembly releasably couplable to the gantry between the x-ray tube and the compression platform, the biopsy guidance assembly comprising:

a first handle and a second handle, wherein at least one of the first handle and the second handle comprises a coupling mechanism to releasably couple the biopsy guidance assembly to the gantry;

a support structure extending between the first handle and the second handle;

a fixed support arm coupled to the support structure;

an angular support arm coupled to the fixed support arm, wherein the angular support arm extends at an angle offset from the plane of the x-ray receptor; and a holster mount moveably coupled to the angular support arm, wherein the holster mount is configured to support a biopsy device having a needle and adapted to position the needle proximate a target location of the breast at the angle of the angular support arm, and wherein when the biopsy guidance assembly is coupled to the gantry, the holster mount is positioned outside of an x-ray field of the x-ray tube so that image artifacts by the holster mount are not formed in the x-ray image data.

2. The upright x-ray mammography imaging system of claim 1, wherein the holster mount is configured to be manually advanced along the angular support arm.

3. The upright x-ray mammography imaging system of claim 1, wherein the angle between the fixed support arm and the angular support arm is adjustable.

4. The upright x-ray mammography imaging system of claim 1, further comprising a lateral biopsy arm, couplable to the biopsy guidance assembly, for supporting the biopsy device during lateral biopsies.

5. The upright x-ray mammography imaging system of claim 1, wherein the biopsy guidance assembly further comprises a needle support coupled to the angular support arm for stabilizing an end of the needle.

6. The upright x-ray mammography imaging system of claim 1, wherein the biopsy guidance assembly further comprises a display configured to display information related to a biopsy procedure.

7. The upright x-ray mammography imaging system of claim 6, wherein the display is removably positionable to each of the first handle and the second handle.

8. The upright x-ray mammography imaging system of claim 1, further comprising a control unit coupled in communication with the gantry, wherein the x-ray image data acquired by the upright x-ray mammography imaging system is used to determine coordinates of the target location for positioning the holster mount.

9. The upright x-ray mammography imaging system of claim 8, wherein the x-ray image data comprises two dimensional image data including at least one of a scout image, a mammogram, a stereotactic image, and a tomosynthesis projection image.

10. The upright x-ray mammography imaging system of claim 8, wherein the x-ray image data comprises three dimensional image data including at least one of stereotactic volume data and tomosynthesis reconstruction data.

11. The upright x-ray mammography imaging system of claim 8, wherein the x-ray image data comprises a combination of two dimensional image data and three dimensional image data.

12. The upright x-ray mammography imaging system of claim 1, further comprising a control unit coupled in communication with the gantry, wherein the control unit includes a display for displaying information associated with the biopsy guidance assembly.

13. The upright x-ray mammography imaging system of claim 1, wherein the biopsy guidance assembly is positioned in a cranial-caudal orientation over the breast.

14. A method of performing a breast biopsy using an upright x-ray mammography imaging system including a gantry, an x-ray tube rotatably supported on the gantry and configured to rotate relative to the gantry over an angular range, a compression platform coupled to the gantry, an x-ray receptor disposed within the compression platform and positioned in a plane normal to the x-ray tube when the x-ray tube is at a zero position on the gantry, and a compression paddle releasably couplable onto the gantry and spaced apart from each of the x-ray tube and the compression platform, the method comprising:

compressing a breast of a patient between the compression paddle and the compression platform;

coupling a biopsy guidance assembly to the gantry between the x-ray tube and the compression platform, wherein the biopsy guidance assembly includes a first handle and a second handle, wherein at least one of the first handle and the second handle includes a coupling mechanism for releasably coupling the biopsy guidance assembly to the gantry, a support structure extending between the first handle and the second handle, a fixed support arm coupled to the support structure, an angular support arm coupled to the fixed support arm, wherein the angular support arm extends at an angle offset from the plane of the x-ray receptor, and a holster mount moveably coupled to the angular support arm;

visualizing a lesion in the breast via emission of an x-ray from the x-ray tube and receiving the emitted x-ray at the x-ray receptor for the generation of x-ray image data, wherein the holster mount is positioned outside of an x-ray field of the x-ray tube so that image artifacts by the holster mount are not formed in the x-ray image data;

targeting the visualized lesion including determining coordinates of the lesion within the compressed breast;

advancing a needle of a biopsy device supported on the holster mount towards the targeted lesion at the angle of the angular support arm; and excising the lesion.

15. The method of claim 14, wherein advancing the needle of the biopsy device includes manually advancing the holster mount along the angular support arm.

16. The method of claim 14, further comprising adjusting the angle between the fixed support arm and the angular support arm.

17. The method of claim 14, wherein the steps of visualizing and targeting are performed using different x-ray image data.

18. The method of claim 17, wherein the x-ray image data comprises two dimensional image data including at least one of a scout image, a mammogram, a stereotactic image, and a tomosynthesis projection image.

19. The method of claim 17, wherein the x-ray image data comprises three dimensional image data including at least one of stereotactic volume data and tomosynthesis reconstruction data.

20. The method of claim 14, further comprising displaying information associated with the breast biopsy on a display of the upright x-ray mammography imaging system.

* * * * *